(12) United States Patent
Lancaster et al.

(10) Patent No.: US 11,890,395 B2
(45) Date of Patent: Feb. 6, 2024

(54) THREE DIMENSIONAL TISSUE COMPOSITIONS AND METHODS OF USE

(71) Applicant: Avery Therapeutics, Inc., Tucson, AZ (US)

(72) Inventors: Jordan J. Lancaster, Tucson, AZ (US); Steven Goldman, Tucson, AZ (US); Jennifer Watson Koevary, Tucson, AZ (US)

(73) Assignee: AVERY THERAPEUTICS, INC., Tucson, AZ (US)

( * ) Notice: Subject to any disclaimer, the term of this patent is extended or adjusted under 35 U.S.C. 154(b) by 0 days.

(21) Appl. No.: 16/010,120

(22) Filed: Jun. 15, 2018

(65) Prior Publication Data

US 2018/0361025 A1  Dec. 20, 2018

Related U.S. Application Data

(60) Provisional application No. 62/521,137, filed on Jun. 16, 2017.

(51) Int. Cl.
| | |
|---|---|
| *A61L 27/36* | (2006.01) |
| *A61L 27/38* | (2006.01) |
| *A61L 27/58* | (2006.01) |
| *A61L 27/56* | (2006.01) |
| *A61L 27/22* | (2006.01) |
| *A61L 27/34* | (2006.01) |

(52) U.S. Cl.
CPC .......... *A61L 27/3633* (2013.01); *A61L 27/22* (2013.01); *A61L 27/34* (2013.01); *A61L 27/3691* (2013.01); *A61L 27/383* (2013.01); *A61L 27/3804* (2013.01); *A61L 27/3808* (2013.01); *A61L 27/3821* (2013.01); *A61L 27/3826* (2013.01); *A61L 27/3834* (2013.01); *A61L 27/56* (2013.01); *A61L 27/58* (2013.01); *A61L 27/367* (2013.01); *A61L 27/3873* (2013.01); *A61L 2300/604* (2013.01); *A61L 2300/606* (2013.01); *A61L 2300/64* (2013.01); *A61L 2420/00* (2013.01); *A61L 2430/20* (2013.01); *A61L 2430/40* (2013.01)

(58) Field of Classification Search
CPC ............................. A61L 27/3633; A61K 9/00
See application file for complete search history.

(56) References Cited

U.S. PATENT DOCUMENTS

| | | | |
|---|---|---|---|
| 4,079,038 A | 3/1978 | Choi et al. | |
| 4,093,709 A | 6/1978 | Choi et al. | |
| 4,131,648 A | 12/1978 | Choi et al. | |
| 4,138,344 A | 2/1979 | Choi et al. | |
| 4,180,646 A | 12/1979 | Choi et al. | |
| 4,304,767 A | 12/1981 | Heller et al. | |
| 4,946,931 A | 8/1990 | Heller et al. | |
| 4,963,489 A | 10/1990 | Naughton et al. | |
| 5,266,480 A | 11/1993 | Naughton et al. | |
| 5,443,950 A | 8/1995 | Naughton et al. | |
| 5,763,267 A | 6/1998 | Kurjan et al. | |
| 5,785,964 A | 7/1998 | Naughton et al. | |
| 5,792,603 A | 8/1998 | Dunkelman et al. | |
| 5,843,766 A | 12/1998 | Applegate et al. | |
| 5,846,828 A | 12/1998 | Peterson et al. | |
| 5,855,610 A * | 1/1999 | Vacanti ................... | A61L 27/18 623/2.13 |
| 5,863,531 A | 1/1999 | Naughton et al. | |
| 5,957,972 A | 9/1999 | Williams et al. | |
| 5,962,325 A | 10/1999 | Naughton et al. | |
| 5,968,543 A | 10/1999 | Heller et al. | |
| 5,858,721 A | 12/1999 | Naughton et al. | |
| 6,291,240 B1 | 9/2001 | Mansbridge et al. | |
| 6,413,536 B1 | 7/2002 | Gibson et al. | |
| 6,596,296 B1 | 7/2003 | Nelson et al. | |
| 6,613,355 B2 | 9/2003 | Ng et al. | |
| 6,667,371 B2 | 12/2003 | Ng et al. | |
| 7,029,838 B2 | 4/2006 | Williams et al. | |
| 7,052,829 B2 | 5/2006 | Williams et al. | |
| 7,775,965 B2 * | 8/2010 | McFetridge ........ | A61L 27/3604 600/36 |

(Continued)

FOREIGN PATENT DOCUMENTS

| | | |
|---|---|---|
| EP | 1930411 | 6/2008 |
| EP | 2422823 A1 | 2/2012 |

(Continued)

OTHER PUBLICATIONS

Landa et al. "Effect of Injectable Alginate Implant on Cardiac Remodeling and Function after Recent and Old Infarct in Rat", (2008), Circulation, vol. 117: 1388-1396. (Year: 2008).*
Perets et al. "Enhancing the vascularization of three-dimensional porous alginate scaffolds by incorporating controlled release basic fibroblast growth factor microspheres" (2003), J of Biomed Mat Res., vol. 65A(4): 489-497. (Year: 2003).*
Koch et al. "Fibrin-polylactide-based tissue-engineered vascular graft in the arterial circulation" (2010) Biomaterials, vol. 31: 4731-4739. (Year: 2010).*
Hart et al. "Dermagraft: Use in the Treatment of Chronic Wounds" (2011), Advances in Wound Care, vol. 1, (3) 138-141. (Year: 2011).*

(Continued)

*Primary Examiner* — Teresa E Knight
(74) *Attorney, Agent, or Firm* — NGUYEN TARBET LLC

(57) ABSTRACT

Engineered tissue compositions for supporting cell growth, maintenance, and/or differentiation featuring a scaffold, extracellular matrix (ECM) material, and optionally a population of ECM-generating cells such as fibroblasts. The tissue compositions may be used for supporting seeded cells of a particular cell type of interest such as cells related to skeletal muscle, smooth muscle, cardiac tissue, gastrointestinal tissue, etc. The tissue compositions with seeded cells may develop into functional tissues, which may have the potential to provide a tissue graft for therapeutic purposes or a valuable model for in vitro assays.

7 Claims, 6 Drawing Sheets
(3 of 6 Drawing Sheet(s) Filed in Color)

(56) References Cited

U.S. PATENT DOCUMENTS

| | | |
|---|---|---|
| 8,802,144 B2 | 8/2014 | Schmuck et al. |
| 9,051,550 B2 | 6/2015 | Lancaster et al. |
| 9,119,831 B2 | 9/2015 | Kentner et al. |
| 9,587,222 B2 | 3/2017 | Matsuda et al. |
| 9,976,123 B2 | 5/2018 | Lancaster et al. |
| 2005/0238624 A1 | 10/2005 | Rabinovsky et al. |
| 2007/0092492 A1 | 4/2007 | Matsuda et al. |
| 2008/0075750 A1 | 3/2008 | Akins, Jr. |
| 2008/0145344 A1 | 6/2008 | Deshpande et al. |
| 2009/0269316 A1* | 10/2009 | Naughton ............... A61P 9/10 424/93.7 |
| 2010/0316701 A1 | 12/2010 | Sussman et al. |
| 2011/0293666 A1 | 12/2011 | Wang et al. |
| 2012/0100114 A1* | 4/2012 | Gregory ............... A61K 35/28 424/93.7 |
| 2012/0264689 A1 | 10/2012 | Mize |
| 2013/0116789 A1 | 5/2013 | Chachques et al. |
| 2014/0178450 A1 | 6/2014 | Christman et al. |
| 2014/0277576 A1 | 9/2014 | Landgrebe et al. |
| 2014/0314869 A1 | 10/2014 | Caplan |
| 2015/0086605 A1* | 3/2015 | Mauney ............... A61L 27/3604 424/426 |
| 2016/0201089 A1 | 7/2016 | Gersbach et al. |
| 2016/0250384 A1 | 9/2016 | Lancaster et al. |
| 2016/0256497 A1 | 9/2016 | Siani-Rose et al. |
| 2017/0136069 A1 | 5/2017 | Hedrick et al. |
| 2018/0223259 A1 | 8/2018 | Lancaster et al. |
| 2018/0282726 A1 | 10/2018 | Bertram et al. |

FOREIGN PATENT DOCUMENTS

| | | | |
|---|---|---|---|
| JP | 2011115058 A | 6/2011 | |
| JP | 2012523238 A | 10/2012 | |
| JP | 2020521483 A | 7/2020 | |
| NO | 2010012127 | 2/2010 | |
| WO | 1996008213 | 3/1996 | |
| WO | WO1996008213 A1 | 3/1996 | |
| WO | 1997049434 A2 | 12/1997 | |
| WO | WO1997049434 A2 | 12/1997 | |
| WO | 1999000152 | 1/1999 | |
| WO | WO1999000152 A3 | 1/1999 | |
| WO | 2000034442 | 6/2000 | |
| WO | 2000035372 | 6/2000 | |
| WO | WO2000034442 A2 | 6/2000 | |
| WO | WO2000035372 A2 | 6/2000 | |
| WO | 200061204 | 10/2000 | |
| WO | WO200061204 A2 | 10/2000 | |
| WO | 2002058588 | 8/2002 | |
| WO | WO2002058588 A2 | 8/2002 | |
| WO | 2003061455 | 7/2003 | |
| WO | WO2003061455 A2 | 7/2003 | |
| WO | 2004030706 | 4/2004 | |
| WO | WO2004030706 A2 | 4/2004 | |
| WO | 2004101735 | 11/2004 | |
| WO | WO2004101735 A2 | 11/2004 | |
| WO | 2006001778 | 1/2006 | |
| WO | WO2006001778 | 1/2006 | |
| WO | 2005094729 | 10/2006 | |
| WO | WO2005094729 A1 | 10/2006 | |
| WO | WO2007/092902 A2 | 8/2007 | |
| WO | WO2007092902 A2 | 8/2007 | |
| WO | 2009099570 | 8/2009 | |
| WO | WO2009099570 A2 | 8/2009 | |
| WO | 2010011407 | 1/2010 | |
| WO | WO2010011407 A2 | 1/2010 | |
| WO | WO2010012127 | 2/2010 | |
| WO | WO2010042856 A2 | 4/2010 | |
| WO | 2010118352 | 10/2010 | |
| WO | 2010118352 A1 | 10/2010 | |
| WO | WO2010118352 | 10/2010 | |
| WO | WO2009102967 A2 | 8/2011 | |
| WO | WO2011102991 A1 | 8/2011 | |
| WO | WO2013/036708 A2 | 3/2013 | |
| WO | WO2013036708 A2 | 3/2013 | |
| WO | WO2014039427 A1 | 3/2013 | |
| WO | WO2013151755 A1 | 10/2013 | |
| WO | WO2014/039429 A1 | 3/2014 | |
| WO | WO2014039427 A1 | 3/2014 | |
| WO | WO2014039429 A1 | 3/2014 | |
| WO | WO2014186755 A2 | 11/2014 | |
| WO | WO-2014186755 A2 * | 11/2014 | ........... C12N 5/0657 |
| WO | WO2015054383 | 4/2015 | |
| WO | WO2015054383 A1 | 4/2015 | |
| WO | 2016167332 A1 | 10/2016 | |
| WO | 2016176559 A1 | 11/2016 | |
| WO | WO2018220179 A1 | 6/2018 | |
| WO | 2018220179 A1 | 12/2018 | |
| WO | WO2020092321 A1 | 5/2020 | |

OTHER PUBLICATIONS

Yeo et al. "Histologic Changes of mpanted Gore Bio-A in an Experimental Animal Model", (2014), BioMed Res Intern'l, vol. 2014: article ID 167962: 1-8. (Year: 2014).*

Gore Bio-A Tissue Reinforcement, Gore product information. (Year: 2014).*

Eitan et al. "Acellular cardiac extracellular matrix as a scaffold for tissue engineering: in vitro 15 cell support, remodeling, and biocompatibility," Tissue Eng Part C Methods, Nov. 3, 2009 (Nov. 3, 2009), vol. 16, No. 4, pp. 671-683.

Li et al., Survival and function of bioengineered cardiac grafts. Circulation, vol. 100 (1999) pp. II-63 to II-69.

Cellnest. http://www.fujifilm.com/products/biomaterials/rcp/.

Information Disclosure Statement for U.S. Appl. No. 14/718,309, submitted on May 21, 2015.

Shiba, et al., "Cardiac Applications for Human Pluripotent stem cells," Current pharmaceutical Design, 15(24): 2791-2806, Aug. 2009.

Ameen, C., et al. (2008), Critical Reviews in Oncology/Hematology, "Human embryonic stem cells: Current technologies and emerging industrial applications." 65(1),54-80.

Barile et al., Cardiac stem cells: isolation, expansion and experimental use for myocardial regeneration. Nat. Clin. Prac. Cardiovasc. Med. Feb. 4, 2007, Suppl 1: S9-S14.

Ben-Shoshan, J. and J. George (2007). "Endothelial progenitor cells as therapeutic vectors in cardiovascular disorders: From experimental models to human trials." Pharmacology & Therapeutics 115(1): 25-36.

Christman, K. L. and R. J. Lee (2006). "Biomaterials for the Treatment of Myocardial Infarction." Journal of the American College of Cardiology 48(5): 907-913.

Dar, A., M. Shachar et al. (2002). "Cardiac tissue engineering Optimization of cardiac cell seeding and distribution in 3D porous alginate scaffolds." Biotechnology and bioengineering 80(3): 305-312.

Fitzpatrick, J. R., et al. (2010). "Tissue-engineered pro-angiogenic fibroblast scaffold improves myocardial perfusion and function and limits ventricular remodeling after infarction." The Journal of Thoracic and Cardiovascular Surgery D 140(3): 667-676.

Gangatirkar et al. (2007), "Establishment of 3D organotypic cultures using human neonatal epidermal cells." Nature Protocols, 2(1): 178-186.

Guo, et al. (2006). "Engineering Cardiac Tissue from Embryonic Stem Cells." Methods in Enzymology, Academic Press. vol. 420: 316-338.

International Search Report for PCT Appl. No. PCT/US10/30579, dated Jul. 12, 2010.

Kellar et al. (2001) Circulation, 104(7):2063-2068.

Kellar et al. (2005) Tissue Engineering, 11(11-12):1678-1687.

Lancaster et al. (2008). "Treatment of Acute Myocardial Infarction Versus Heart Failure with a Viable 3-Dimensional Fibroblast Patch." Journal of Cardiac Failure 14 (6, Supplement 1): S54-S54.

Lancaster et al. (2009). "Construction of a Spontaneously Contracting Biologically Active Cardiomyocyte Scaffold." Journal of Cardiac Failure 15(6, Supplement 1): S44-S45.

Lancaster et al. (2010). "In Vivo Evaluation of a Biologically Active Cardiomyocyte Seeded Scaffold." Journal of Cardiac Failure 16(8, Supplement 1): S45-S45.

(56) References Cited

OTHER PUBLICATIONS

Ma et al. (2009). "Differentiation of bone marrow-derived mesenchymal stem cells into multilayered epidermis-like cells in 3D organotypic coculture." Biomaterials 30(19): 3251-3258.
M. Buja et al. (2008). "Cardiomyocyte death and renewal in the normal and diseased heart." Cardiovascular Pathology 17(6): 349-374.
Menasche, P. (2008). "Current Status and Future Prospects for Cell Transplantation to Prevent Congestive Heart Failure." Seminars in Thoracic and Cardiovascular Surgery 20(2): 131-137.
Messina et al., Circulation Research, 2004, 95:911.
Mizuno et al. (2004). "Hydrostatic fluid pressure promotes cellularity and proliferation of human dermal fibroblasts in a three-dimensional collagen gel/sponge." Biochemical Engineering Journal 20(2-3): 203-208.
Newton et al., Blood flow changes in diabetic foot ulcers treated with dermal replacement therapy. 2002, J Foot Ankle Surg, 41(4):233-7.
Noort et al., Stem Cells from In- or Outside of the Heart: Isolation, Characterization, and Potential for Myocardial Tissue Regeneration. Pediatric Cardiology, 30(5):699 (2009).
Pullens et al. (2009). "The influence of endothelial cells on the ECM composition of 3D engineered cardiovascular constructs." Journal of tissue engineering and regenerative medicine 3(1): 11-18.
Radisic et al. (2008). "Pre treatment of synthetic elastomeric scaffolds by cardiac fibroblasts improves engineered heart tissue." Journal of Biomedical Materials Research Part A 86(3): 713-724.
Radisic et al. (2003). "High-density seeding of myocyte cells for cardiac tissue engineering." Biotechnology and bioengineering 82(4): 403-414.
Rennekampff et al. (1996). "Integrin and matrix molecule expression in cultured skin replacements." Journal of Burn Care & Research 17(3): 213.
Schmidt et al. (2006). "Mesenchymal stem cells transmigrate over the endothelial barrier." European Journal of Cell Biology 85(11): 1179-1188.
Shapira-Schweitzer, et al. (2009). "A photopolymerizable hydrogel for 3-D culture of human embryonic stem cell-derived cardiomyocytes and rat neonatal cardiac cells." Journal of Molecular and Cellular Cardiology 46(2): 213-224.
Takei et al. (1993). "Thermal expansion behavior of skeletonized 3D-composites." Materials Science and Engineering: A 161(2): 213-220.
Thai et al. (2007). "The Use of a Viable, Biodegradable 3-Dimensional Fibroblast Construct (3DFC) in Acute and Chronic Heart Failure." Journal of Cardiac Failure 13(6, Supplement 2): SI21-S121.
Uchino et al. (2009). "Reconstruction of three-dimensional human skin model composed of dendritic cells, keratinocytes and fibroblasts utilizing a handy scaffold of collagen vitrigel membrane." Toxicology in Vitro 23(2): 333-337.
Wang et al. (2010). "Cellular cardiomyoplasty and cardiac tissue engineering for myocardial therapy." Advanced Drug Delivery Reviews 62(7-8): 784-797.
Wu et al. (2007). "Stem cells for tissue engineering of myocardial constructs." Ageing Research Reviews 6(4): 289-301.
Matsui et al., "Akt activation preserves cardiac function and prevents injury after transient cardiac ischemia in vivo" Circulation (2001) vol. 10 4, pp. 330-335.
Carrier et al., "Cardiac tissue engineering: cell seeding, cultivation parameters, and tissue construct characterization" Biotechnology and Bioengineering (1999) vol. 64(5), pp. 580-589.
Michael Siani-Rose: "Theregen, Inc.", Regenerative Medicine, vol. 1, No. 6, Nov. 1, 2006 (Nov. 1, 2006), pp. 841-846, XP055770928, GB ISSN: 1746-0751, DOI: 10.2217/17460751.1.6.841.
Baharvand H et al: "The effect of extracellular matrix on embryonic stem cell-derived cardiomyocytes", Journal of Molecular and Cellular Cardiology, Academic Press, GB, vol. 38, No. 3, Mar. 1, 2005 (Mar. 1, 2005), pp. 495-503, DOI: 10.1016/J.YJMCC.2004.12.011.

Eitan et al. "Acellular cardiac extracellular matrix as a scaffold for tissue engineering: in vitro cell support, remodeling, and biocompatibility," Tissue Eng Part C Methods, Nov. 3, 2009, vol. 16 No. 4 pp. 671-683. Entire Document.
Alrubaiy et al. Skin Substitutes: A Brief Review of Types and Clinical Applications. Oman Medical Journal 2009, vol. 24, Issue 1, Jan. 2009.
Li et al., "Survival and function of bioengineered cardiac grafts." Circulation, vol. 100 (1999) pp. 11-63 to li-69.
Zakharova, et al., "Transplantation of cardiac progenitor cell sheet onto infarcted heart promotes cardiogenesis and improves function," Cardiovascular Research, 87(1 ): 40-49, Jan. 2010.
Christman, et al. "Biomaterials for the treatment of myocardial infarction." Journal of the American College of Cardiology 48.5 (2006): 907-913.
Dar et al. "Optimization of cardiac cell seeding and distribution in 3D porous alginate scaffolds." Biotechnology and bioengineering 80.3 (2002): 305-312.
Fitzpatrick et al. "Tissue-engineered pro-angiogenic fibroblast scaffold improves myocardial perfusion and function and limits ventricular remodeling after infarction." The Journal of thoracic and cardiovascular surgery 140.3 (2010): 667-676.
Gangatirkar et al. "Establishment of 3D organotypic cultures using human neonatal epidermal cells." Nature protocols 2.1 (2007): 178-186.
Mansbridge, Commercial considerations in tissue engineering. J_Anal. (2006) 209, pp. 527-532.
Kellar et al. "Scaffold-based three-dimensional human fibroblast culture provides a structural matrix that supports angiogenesis in infarcted heart tissue." Circulation 104.17 (2001): 2063-2068.
Kellar et al. "Cardiac patch constructed from human fibroblasts attenuates reduction in cardiac function after acute infarct." Tissue engineering 11.11-12 (2005): 1678-1687.
Lancaster et al. "Treatment of Acute Myocardial Infarction Versus Heart Failure with a Viable 3-Dimensional Fibroblast Patch." Journal of Cardiac Failure 14.6 (2008): S54.
Lancaster et al. "Construction of a spontaneously contracting biologically active cardiomyocyte scaffold." Journal of Cardiac Failure 15.6 (2009): S44-S45.
Lancaster et al. "In Vivo Evaluation of a Biologically Active Cardiomyocyte Seeded Scaffold." Journal of Cardiac Failure 16.8 (2010): S45.
Martinez et al. "Adult stem cells for cardiac tissue engineering." Journal of Molecular and Cellular Cardiology Feb. 2011 vol. 50, Issue 2, pp. 312-319.
Messina et al. "Isolation and expansion of adult cardiac stem cells from human and murine heart." Circulation research 95.9 (2004): 911-921.
Newton et al. "Blood flow changes in diabetic foot ulcers treated with dermal replacement therapy." The Journal of foot and ankle surgery 41.4 (2002): 233-237.
Radisic et al. "Pre-treatment of synthetic elastomeric scaffolds by cardiac fibroblasts improves engineered heart tissue." Journal of biomedical materials research Part A 86.3 (2008): 713-724.
Thai et al. "The Use of a Viable, Biodegradable 3-Dimensional Fibroblast Construct (3DFC) in Acute and Chronic Heart Failure." Journal of Cardiac Failure 13.6 (2007): S121.
Matsui et al. "Akt activation preserves cardiac function and prevents injury after transient cardiac ischemia in vivo." Circulation 104.3 (2001): 330-335.
Carrier et al. "Cardiac tissue engineering: cell seeding, cultivation parameters, and tissue construct characterization." Biotechnology and bioengineering 64.5 (1999): 580-589.
Siani-Rose: "Theregen, Inc.", Regenerative Medicine, vol. 1, No. 6, Nov. 1, 2006 {Nov. 1, 2006), pp. 841-846, XP055770928, GB ISSN: 1746-0751, DOI:0.2217/17460751.1.6.841.
Landa et al. "Effect of injectable alginate implant on cardiac remodeling and function after recent and old infarcts in rat." Circulation 117.11 (2008): 1388-1396.
Thai et al. "Implantation of a Three-Dimensional Fibroblast Matrix Improves Left Ventricular Function and Blood Flow After Acute Myocardial Infarction" 2009 ; 18(3): 283-295.

(56) References Cited

OTHER PUBLICATIONS

Decision of Dismissal of Amendment dated May 9, 2023 for corresponding JP patent application 2020-519013.
Nakano, Shigeyuki. "Biodegradable fiber." Sen-I Gakkaishi 62.11 (2006): p. 330-p. 333.
Examination report No. 1 for your standard patent application dated Jun. 16, 2023 for corresponding AU patent application 2018283372.

* cited by examiner

FIG. 1

| Example | Scaffold | ECM | ECM-Generating Cells or Non-ECM-Generating Cells | Seeded Cells | Additional Factors |
|---|---|---|---|---|---|
| 1 | ✓ | ✓ | | | |
| 2 | ✓ | ✓ | ✓ | | |
| 3 | ✓ | ✓ | | ✓ | |
| 4 | ✓ | ✓ | ✓ | ✓ | |
| 5 | ✓ | ✓ | ✓ | | ✓ |
| 6 | ✓ | ✓ | | | ✓ |
| 7 | ✓ | ✓ | | ✓ | ✓ |

FIG. 2

| Example | Absorbable Fibers | Non-Absorbable Fibers | Sponge/Film | Biological Material | Synthetic Material | Material for Enhancing Cell or ECM Adherence |
|---|---|---|---|---|---|---|
| 1 | ✓ | | | ✓ | | |
| 2 | | ✓ | | | ✓ | |
| 3 | ✓ | | | | ✓ | |
| 4 | ✓ | ✓ | | | ✓ | |
| 5 | ✓ | ✓ | | ✓ | ✓ | |
| 6 | ✓ | | | ✓ | ✓ | |
| 7 | ✓ | | | ✓ | | ✓ |
| 8 | ✓ | ✓ | | ✓ | ✓ | ✓ |
| 9 | ✓ | | | ✓ | ✓ | ✓ |
| 10 | | | | ✓ | | |
| 11 | ✓ | | | | | |
| 12 | | ✓ | | | | |
| 13 | | | ✓ | ✓ | | |
| 14 | | | ✓ | ✓ | | ✓ |
| 15 | ✓ | | ✓ | ✓ | | |
| 16 | | ✓ | ✓ | ✓ | | |
| 17 | ✓ | | ✓ | ✓ | ✓ | |
| 18 | | ✓ | ✓ | ✓ | ✓ | |
| 19 | ✓ | | ✓ | ✓ | | ✓ |
| 20 | ✓ | ✓ | ✓ | ✓ | ✓ | ✓ |

| Example | Material Derived from ECM-generating cells | | Synthetic ECM | Additional Factors | | | Cells | | |
|---|---|---|---|---|---|---|---|---|---|
| | WT ECM-Generating Cells | GM ECM-Generating Cells | | Growth Factors, etc. | Drugs | Cell Adherence Features | Live | Dead | Cell Free |
| 1 | | | ✓ | | | | | | ✓ |
| 2 | ✓ | | | | | | ✓ | ✓ | |
| 3 | ✓ | | | | | | ✓ | | |
| 4 | ✓ | | | | | | | ✓ | |
| 5 | ✓ | ✓ | | | | | | ✓ | |
| 6 | ✓ | ✓ | | | | | ✓ | | |
| 7 | ✓ | ✓ | | | | | ✓ | ✓ | |
| 8 | | ✓ | | | | | | ✓ | |
| 9 | | ✓ | | | | | ✓ | | |
| 10 | | ✓ | | | | | ✓ | ✓ | |
| 11 | ✓ | | ✓ | | | | ✓ | | |
| 12 | ✓ | | | ✓ | | | ✓ | | |
| 13 | | ✓ | ✓ | ✓ | | | ✓ | ✓ | |
| 14 | ✓ | ✓ | | ✓ | | ✓ | ✓ | | |
| 15 | ✓ | ✓ | | ✓ | ✓ | ✓ | ✓ | | |
| 16 | ✓ | | | | | ✓ | ✓ | ✓ | |
| 17 | | ✓ | | ✓ | ✓ | | | | |
| 18 | ✓ | | | ✓ | ✓ | ✓ | ✓ | | |
| 19 | ✓ | | ✓ | ✓ | | | ✓ | | |
| 20 | | ✓ | | | ✓ | | | ✓ | |
| 21 | ✓ | ✓ | | | ✓ | | | ✓ | |
| 22 | ✓ | | | | | ✓ | ✓ | ✓ | |
| 23 | ✓ | | ✓ | ✓ | | | ✓ | ✓ | |

FIG. 6

| Example | Wild Type | Genetically Modified | Disease-derived or Mutant | Proliferative | Non-Proliferative | ECM-Generating Cells | Stem cells/ Progenitor Cells | Differentiated Cells | Additional Factors (e.g., growth factors, drugs, enhancement cells, etc.) |
|---|---|---|---|---|---|---|---|---|---|
| 1 | ✔ | | | | | | | | |
| 2 | | ✔ | | | | | | | |
| 3 | | | ✔ | | | | | | |
| 4 | ✔ | ✔ | | | | | | | |
| 5 | ✔ | | ✔ | | | | | | |
| 6 | ✔ | | | | | | ✔ | | |
| 7 | | ✔ | | | | | | ✔ | |
| 8 | | | ✔ | | ✔ | | | ✔ | |
| 9 | ✔ | ✔ | | | | | | | |
| 10 | ✔ | | ✔ | | | | | | |
| 11 | ✔ | | | | | | ✔ | | ✔ |
| 12 | | ✔ | | | | | | ✔ | ✔ |
| 13 | | | ✔ | | ✔ | | | | ✔ |
| 14 | ✔ | | | ✔ | | | ✔ | | |
| 15 | | ✔ | | ✔ | | | ✔ | | |
| 16 | ✔ | | | | | ✔ | | | |
| 17 | | ✔ | | | | ✔ | | | |
| 28 | ✔ | ✔ | | | | ✔ | | | |
| 19 | ✔ | | ✔ | | | ✔ | | | |
| 20 | ✔ | | | | | ✔ | ✔ | | |
| 21 | | ✔ | | | | ✔ | | ✔ | |
| 22 | | | ✔ | | ✔ | ✔ | | ✔ | |
| 23 | ✔ | ✔ | | | | ✔ | | | |
| 24 | ✔ | | ✔ | | | ✔ | | | |
| 25 | ✔ | | | | | ✔ | ✔ | | ✔ |
| 26 | | ✔ | | | | ✔ | | ✔ | ✔ |
| 27 | | | ✔ | | ✔ | ✔ | | | ✔ |

THREE DIMENSIONAL TISSUE COMPOSITIONS AND METHODS OF USE

CROSS REFERENCE

This application claims priority to U.S. Provisional Patent Application No. 62/521,137 filed Jun. 16, 2017, the specification(s) of which is/are incorporated herein in their entirety by reference.

FIELD OF THE INVENTION

The present invention relates to tissue engineering, more particularly to three-dimensional engineered tissue compositions for allowing growth, differentiation, and/or maintenance of one or more cell types. The tissue compositions herein may be constructed for in vitro or in vivo use, e.g., implantation or surgical purposes. The tissue compositions herein may be adapted for short-term storage or long-term storage (e.g., cryopreservation).

BACKGROUND OF THE INVENTION

In recent years, three-dimensional cultures have been increasingly used to provide conditions similar to what would be expected in vivo (e.g., an appropriate structure and microenvironment) for cell growth, differentiation, and/or maintenance. A great deal of effort is currently focused on developing three-dimensional cultures that mimic specific tissues. Such three-dimensional tissue cultures may be used for a variety of purposes, such as for therapeutic purposes, for generating biological models for research and testing, etc.

SUMMARY OF THE INVENTION

The present invention features engineered tissue compositions, e.g., three-dimensional tissue compositions that support cell growth, maintenance, and/or differentiation, etc. The tissue compositions herein may be used for a variety of purposes including in vitro applications and in vivo applications, e.g., therapeutic purposes such as surgical implantation for the purpose of treating a disease or condition.

For example, the present invention provides a tissue composition comprising a scaffold (a scaffold described herein) and extracellular matrix (ECM) material disposed on or on and within the scaffold. The ECM may be biologically-derived (e.g., produced by ECM-generating cells), synthetically-derived, or feature a portion that is biologically-derived and a portion that is synthetically-derived. Other features of the tissue composition are described below.

The present invention provides a tissue composition comprising a scaffold (a scaffold described herein) and extracellular matrix (ECM) material disposed on or on and within the scaffold, wherein the ECM is cell free. The ECM may be biologically-derived (e.g., produced by ECM-generating cells), synthetically-derived, or feature a portion that is biologically-derived and a portion that is synthetically-derived. Other features of the tissue composition are described below.

The present invention also provides a tissue composition comprising a scaffold (a scaffold described herein), and extracellular matrix (ECM) material and ECM-generating cells disposed on or on and within the scaffold. The ECM may be biologically-derived (e.g., produced by ECM-generating cells), synthetically-derived, or feature a portion that is biologically-derived and a portion that is synthetically-derived. Other features of the tissue composition are described below.

The present invention also provides a tissue composition comprising a scaffold with pores therein, wherein at least a portion of the scaffold is constructed from a slow-degrading material, the slow-degrading material is one that resorbs, absorbs, or degrades in a time frame no less than 1 month after initiation of cell culture and/or implantation (e.g., the slow-degrading material does not completely resorb, absorb, or degrade within a month after implantation); and extracellular matrix (ECM) material disposed on the scaffold or on and within the scaffold. The present invention also provides a tissue composition comprising a scaffold with pores therein, wherein at least a portion of the scaffold is constructed from a slow-degrading material, the slow-degrading material is one that resorbs, absorbs, or degrades in a time frame no less than 2 months initiation of cell culture and/or after implantation (e.g., the slow-degrading material does not completely resorb, absorb, or degrade within 2 months after implantation); and extracellular matrix (ECM) material disposed on the scaffold or on and within the scaffold. The present invention also provides a tissue composition comprising a scaffold with pores therein, wherein at least a portion of the scaffold is constructed from a slow-degrading material, the slow-degrading material is one that resorbs, absorbs, or degrades in a time frame no less than 3 months after initiation of cell culture and/or implantation (e.g., the slow-degrading material does not completely resorb, absorb, or degrade within 3 months after implantation); and extracellular matrix (ECM) material disposed on the scaffold or on and within the scaffold. The present invention also provides a tissue composition comprising a scaffold with pores therein, wherein at least a portion of the scaffold is constructed from a slow-degrading material, the slow-degrading material is one that resorbs, absorbs, or degrades in a time frame no less than 6 months after initiation of cell culture and/or implantation (e.g., the slow-degrading material does not completely resorb, absorb, or degrade within 6 months after implantation); and extracellular matrix (ECM) material disposed on the scaffold or on and within the scaffold. In certain embodiments, the slow-degrading material comprises proteins, polymers, or a plurality of fibers. In certain embodiments, the tissue composition does not fold onto itself (e.g., spontaneously fold onto itself) during implantation. In certain embodiments, the tissue composition is not able to remain folded onto itself during if a user accidentally folds the tissue composition onto itself (e.g., during implantation). In certain embodiments, at least a portion of the scaffold is non-resorbable. In some embodiments, the tissue composition has cell layers, wherein the cell layers are from 3 to 500 cell layers thick. In some embodiments, the tissue composition further comprises seeded cells seeded in and/or on the ECM, wherein the seeded cells are stem cells, embryonic stem cells, embryonic stem cell-derived cells, inducible pluripotent stem cell-derived cells, progenitor cells, cardiac cells, a skeletal muscle cells, smooth muscle cells, liver cells, pancreatic cells, lung cells, bone cells, umbilical cord cells, endothelial cells, central nervous system cells, gastrointestinal cells, endocrine cells, salivary cells, mesenchymal stem cells, fibroblast cells, or paracrine cells. In some embodiments, the seeded cells are seeded as spheroids or in the form of a cell sheet, in the form of a gel, or in the form of a foam. Other features of the tissue composition are described below.

The present invention also provides a tissue composition comprising: a scaffold constructed from a plurality of recombinant peptides with pores therein; and extracellular matrix (ECM) material disposed on the scaffold or on and within the scaffold. In some embodiments, the tissue composition further comprises ECM-generating cells in the ECM, wherein the ECM-generating cells are live, dead, or a portion of the ECM-generating cells are dead. In some embodiments, the tissue composition further comprises seeded cells seeded in or on the ECM, the seeded cells are stem cells, embryonic stem cells, embryonic stem cell-derived cells, inducible pluripotent stem cell-derived cells, progenitor cells, cardiac cells, a skeletal muscle cells, smooth muscle cells, liver cells, pancreatic cells, lung cells, bone cells, umbilical cord cells, endothelial cells, central nervous system cells, gastrointestinal cells, endocrine cells, salivary cells, mesenchymal stem cells, fibroblast cells, or paracrine cells. Other features of the tissue composition are described below.

The present invention also provides a tissue composition comprising: a scaffold constructed from a plurality of fibers with pores therein; and extracellular matrix (ECM) material disposed on the scaffold or on and within the scaffold. The present invention also provides a tissue composition comprising: a scaffold constructed from a plurality of fibers with pores therein; extracellular matrix (ECM) material disposed on the scaffold or on and within the scaffold, and seeded cells seeded in and/or on the ECM. In certain embodiments, the seeded cells are stem cells, inducible pluripotent stem cell-derived cells, progenitor cells, cardiac cells, a skeletal muscle cells, smooth muscle cells, liver cells, pancreatic cells, lung cells, bone cells, umbilical cord cells, endothelial cells, central nervous system cells, gastrointestinal cells, endocrine cells, mesenchymal stem cells, fibroblast cells, salivary cells, or paracrine cells. Other features of the tissue composition are described below.

The present invention also provides a tissue composition comprising: a scaffold constructed from a plurality of recombinant peptides with pores therein or a plurality of proteins with pores therein or a plurality of polymers with pores therein; and extracellular matrix (ECM) material disposed on the scaffold or on and within the scaffold. The present invention also provides a tissue composition comprising: a scaffold constructed from a plurality of recombinant peptides with pores therein or a plurality of proteins with pores therein or a plurality of polymers with pores therein; extracellular matrix (ECM) material disposed on the scaffold or on and within the scaffold, and seeded cells seeded in and/or on the ECM. In certain embodiments, the seeded cells are stem cells, inducible pluripotent stem cell-derived cells, progenitor cells, cardiac cells, a skeletal muscle cells, smooth muscle cells, liver cells, pancreatic cells, lung cells, bone cells, umbilical cord cells, endothelial cells, central nervous system cells, gastrointestinal cells, endocrine cells, mesenchymal stem cells, fibroblast cells, salivary cells, or paracrine cells. Other features of the tissue composition are described below.

The present invention also provides a tissue composition comprising: a scaffold constructed from a plurality of fibers with pores therein or a plurality of recombinant peptides with pores therein or a plurality of proteins with pores therein or a plurality of polymers with pores therein; and extracellular matrix (ECM) material disposed on the scaffold or on and within the scaffold. The present invention also provides a tissue composition comprising: a scaffold constructed from a plurality of fibers with pores therein or a plurality of recombinant peptides with pores therein or a plurality of proteins with pores therein or a plurality of polymers with pores therein; extracellular matrix (ECM) material disposed on the scaffold or on and within the scaffold; and seeded cells seeded in and/or on the ECM. In certain embodiments, the seeded cells are stem cells, inducible pluripotent stem cell-derived cells, progenitor cells, cardiac cells, a skeletal muscle cells, smooth muscle cells, liver cells, pancreatic cells, lung cells, bone cells, umbilical cord cells, endothelial cells, central nervous system cells, gastrointestinal cells, endocrine cells, mesenchymal stem cells, fibroblast cells, salivary cells, or paracrine cells. Other features of the tissue composition are described below.

The present invention also provides a tissue composition comprising: a scaffold constructed from a plurality of fibers with pores therein or a plurality of recombinant peptides with pores therein or a plurality of proteins with pores therein or a plurality of polymers with pores therein; extracellular matrix (ECM) material disposed on the scaffold or on and within the scaffold; and seeded cells seeded in and/or on the ECM, wherein the seeded cells are cardiomyocytes. In certain embodiments, the tissue composition has a beat rate from 0-120 bpm. In certain embodiments, the tissue composition has a beat rate from 0-60 bpm. In certain embodiments, the tissue composition has a beat rate from 0-50. In certain embodiments, a drug or solution or other product is applied to the tissue composition to achieve a particular beat rate, e.g., a beat rate from 0-60, 0-50, etc. In certain embodiments, the cardiomyocytes make up from 3 to 60% of the area of the tissue composition or from 3 to 60% of the volume of the tissue composition or from 3 to 60% of the volume of the cellular material in the tissue composition. Other features of the tissue composition are described below.

The present invention also provides a tissue composition comprising: a scaffold constructed from a plurality of fibers with pores therein or a plurality of recombinant peptides with pores therein or a plurality of proteins with pores therein or a plurality of polymers with pores therein; extracellular matrix (ECM) material disposed on the scaffold or on and within the scaffold; and seeded cells seeded in the ECM, wherein the seeded cells are skeletal muscle cells. The present invention also provides a tissue composition comprising: a scaffold constructed from a plurality of fibers with pores therein or a plurality of recombinant peptides with pores therein or a plurality of proteins with pores therein or a plurality of polymers with pores therein; extracellular matrix (ECM) material disposed on the scaffold or on and within the scaffold; and seeded cells seeded in the ECM, wherein the seeded cells are liver cells. The present invention also provides a tissue composition comprising: a scaffold constructed from a plurality of fibers with pores therein or a plurality of recombinant peptides with pores therein or a plurality of proteins with pores therein or a plurality of polymers with pores therein; extracellular matrix (ECM) material disposed on the scaffold or on and within the scaffold; and seeded cells seeded in the ECM, wherein the seeded cells are gastrointestinal cells. The present invention also provides a tissue composition comprising: a scaffold constructed from a plurality of fibers with pores therein or a plurality of recombinant peptides with pores therein or a plurality of proteins with pores therein or a plurality of polymers with pores therein; extracellular matrix (ECM) material disposed on the scaffold or on and within the scaffold; and seeded cells seeded in the ECM, wherein the seeded cells are pancreatic cells. The present invention also provides a tissue composition comprising: a scaffold constructed from a plurality of fibers with pores therein or a plurality of recombinant peptides with pores therein or a plurality of proteins with pores therein or a plurality of polymers with pores therein; extracellular matrix (ECM)

material disposed on the scaffold or on and within the scaffold; and seeded cells seeded in the ECM, wherein the seeded cells are umbilical cord cells or cord blood cells. The present invention also provides a tissue composition comprising: a scaffold constructed from a plurality of fibers with pores therein or a plurality of recombinant peptides with pores therein or a plurality of proteins with pores therein or a plurality of polymers with pores therein; extracellular matrix (ECM) material disposed on the scaffold or on and within the scaffold, and seeded cells seeded in the ECM, wherein the seeded cells are smooth muscle cells. Other features of the tissue compositions are described below.

The present invention also provides a tissue composition comprising a scaffold constructed from a plurality of recombinant peptides forming a sponge-like configuration with pores; and ECM material disposed on or on and throughout the scaffold. In certain embodiments, some the pores overlap. In certain embodiments, the pores are closely spaced. In certain embodiments, the recombinant peptides are collagen type I. In certain embodiments, the recombinant peptides are one or a combination of peptides found in extracellular matrix material.

The present invention also provides a tissue composition comprising at least a scaffold and ECM as described herein, wherein the tissue composition is in a closed culture system (e.g., grown in the closed culture system, maintained in the closed culture system, stored in the closed culture system, e.g., cryopreserved in the closed culture system).

The present invention also provides a tissue composition comprising at least a scaffold and ECM as described herein, wherein the tissue composition is in a cryopreserved state, e.g., from −80° C. to −196° C., −90° C. to −196° C., etc. In certain embodiments, the tissue composition can be in a cryopreserved state for at least 3 days, at least 7 days, at least 14 days, at least 21 days, at least 60 days, at least 3 months, at least 6 months, at least 1 year, at least 2 years, etc.

The following features may be applied to any of the aforementioned tissue compositions previously provided or to any of the tissue compositions described herein, or to any of the methods described herein.

In some embodiments, the ECM is produced prior to its deposition on the scaffold. The ECM may be cell free, e.g., in some embodiments, the ECM is all synthetically-derived. In some embodiments, the ECM is biologically-derived (e.g., produced by ECM-generating cells) and subsequently decellularized. In some embodiments, the ECM is biologically-derived (e.g., produced by ECM-generating cells) and the ECM and ECM-generating cells are seeded on the scaffold. In some embodiments, ECM-generating cells are seeded on the scaffold and the ECM-generating cells subsequently produce the ECM.

In some embodiments, the ECM-generating cells are live cells. In some embodiments, the ECM-generating cells are dead cells. In some embodiments, a portion of the ECM-generating cells is dead. For example, in some embodiments, at least 10%, at least 20%, at least 30%, at least 40%, at least 50%, at least 60%, at least 70%, at least 80%, at least 90%, at least 95%, at least 99% of the ECM-generating cells are dead. In certain embodiments, the density of ECM-generating cells in the scaffold is from $5 \times 10^5$ cells/cm$^2$ to $5 \times 10^7$ cells/cm$^2$. In some embodiments, the ECM-generating cells are genetically modified to express one or more genes.

In some embodiments, the scaffold (or a portion thereof) is constructed from a material that degrades in a time frame no less than 4 weeks after implantation, e.g., the portion of the scaffold that is absorbable/resorbable/degradable degrades in a time frame no less than 4 weeks after implantation. In some embodiments, the scaffold (or a portion thereof) is constructed from a material that degrades in a time frame no less than 1 month after implantation, e.g., the portion of the scaffold that is absorbable/resorbable/degradable degrades in a time frame no less than 1 month after implantation. In some embodiments, the scaffold (or a portion thereof) is constructed from a material that degrades in a time frame no less than 6 weeks after implantation, e.g., the portion of the scaffold that is absorbable/resorbable/degradable degrades in a time frame no less than 6 weeks after implantation. In some embodiments, the scaffold (or a portion thereof) is constructed from a material that degrades in a time frame no less than 8 weeks after implantation, e.g., the portion of the scaffold that is absorbable/resorbable/degradable degrades in a time frame no less than 8 weeks after implantation. In some embodiments, the scaffold (or a portion thereof) is constructed from a material that degrades in a time frame no less than 3 months after implantation, e.g., the portion of the scaffold that is absorbable/resorbable/degradable degrades in a time frame no less than 3 months after implantation. In some embodiments, the scaffold (or a portion thereof) is constructed from a material that degrades in a time frame no less than 4 months after implantation, e.g., the portion of the scaffold that is absorbable/resorbable/degradable degrades in a time frame no less than 4 months after implantation. In some embodiments, the scaffold (or a portion thereof) is constructed from a material that degrades in a time frame no less than 6 months after implantation, e.g., the portion of the scaffold that is absorbable/resorbable/degradable degrades in a time frame no less than 6 months after implantation.

The ECM-generating cells may be fibroblasts, e.g., iPSC-derived fibroblasts, embryonic stem cell-derived fibroblasts, organ-derived fibroblasts (e.g., dermal fibroblasts), etc. In certain embodiments, the ECM-generating cells are non-fibroblasts.

With respect to the scaffold, the scaffold may be constructed from a plurality of fibers with a plurality of pores disposed between the fibers. In certain embodiments, the scaffold is constructed from a plurality or network of proteins. In some embodiments, the scaffold is constructed from a plurality or network of polymers. In certain embodiments, the scaffold is constructed from a plurality or network of recombinant peptides. In certain embodiments, the recombinant peptides are collagen type I. In certain embodiments, the recombinant peptides are one or a combination of ECM-related peptides. In certain embodiments, the recombinant peptides for a sponge-like configuration or film-like configuration. In some embodiments, the pores have a diameter is from 50 μm to 500 μm. In some embodiments, the pores have a diameter from 50 μm to 1000 μm. The pores may be arranged non-uniformly throughout the scaffold. In certain embodiments, at least a portion of the scaffold is resorbable, absorbable, or degradable in a time frame up to 3 years following implantation into a subject. In certain embodiments, the ECM fills in at least 80% of the pores. The tissue composition may be able to lie in a flat orientation. In certain embodiments, the tissue composition can curl. In certain embodiments, cell layers in the tissue composition are from 3 to 500 cell layers thick. In certain embodiments, the scaffold is at least 50 μm thick. In some embodiments, the tissue composition is from 200-1000 μm thick.

The tissue composition may feature seeded cells seeded on or within the scaffold and/or ECM. In certain embodiments, the seeded cells are seeded as a solution. In certain embodiments, the seeded cells are seeded as spheroids. In certain embodiments, the seeded cells are seeded in the form of a cell sheet. In certain embodiments, the seeded cells are seeded in the form of a gel. IN certain embodiments, the seeded cells are seeded in the form of a foam. In some embodiments, the seeded cells are stem cells (e.g., mesenchymal stem cells), inducible pluripotent stem cell-derived cells, progenitor cells, terminally differentiated cells (e.g., hepatocytes, beta cells, endoderm cells, smooth muscle cells, skeletal muscle cells, salivary cells, epithelial cells, endothelial cells, cardiomyocytes, or a combination thereof), or a combination thereof.

The seeded cells may form a layer, wherein the layer is 3 or more cells thick, 4 or more cells thick, 5 or more cells thick, etc. The seeded cells may be derived from a tissue in a diseased or mutant state. The seeded cells may be genetically modified, e.g., modified to express one or more genes.

The tissue composition may have a beat rate from 0-50 bpm. The tissue composition may have a beat rate from 0-120 bpm.

In certain embodiments, the tissue composition can be evaluated for one or more mechanical parameters, electrophysiological parameters, chemical parameters, biochemical parameters, or a combination thereof. Mechanical parameters or Electrophysiological parameters may include but are not limited to contraction rate, contraction/relaxation velocity, force of contraction-paced, force of contraction—not paced, displacement velocity, displacement force, directionality of impulse, velocity of impulse, field potential, amplitude, capture threshold, chronotropic response, activation sequence after stimulation, functional gap junction formation, response to electrical pacing, field potential amplitude, conduction velocity, propagation patterns, gap junction analysis, oxygen consumption, or a combination thereof.

As previously discussed, the tissue composition may be cryopreserved. The tissue composition may retain its structural integrity when cryopreserved and subsequently thawed. The tissue composition may be centrifuged and retain its structural integrity. The composition may maintain its structural integrity when handled with forceps or hands.

The present invention also provides methods of producing or manufacturing tissue compositions herein. The methods may feature the use of any of the scaffolds, ECMs, cells, and other materials or features described herein. In some embodiments, the method may comprise applying extracellular matrix (ECM) material to a scaffold; and seeding a population of seeded cells in the ECM. In some embodiments, the method comprises applying extracellular matrix (ECM) material to a scaffold; seeding a population of ECM-generating cells on and/or in the ECM in the scaffold; and seeding a population of seeded cells on and/or in the ECM. In some embodiments, the method comprises applying extracellular matrix (ECM)-generating cells to a scaffold and culturing said ECM-generating cells to produce ECM in the scaffold. A population of seeded cells may then be seeded on and/or in the ECM.

Regarding the aforementioned methods, in some embodiments, the ECM is produced prior to its deposition on the scaffold. The ECM may be cell-free. In certain embodiments, the ECM is decellularized. In some embodiments, the ECM is produced by ECM-generating cells. In some embodiments, the ECM is synthetically-derived. In some embodiments, a portion of the ECM is biologically-produced and a portion is synthetically produced. In some embodiments, the ECM is seeded with ECM-generating cells, which are cultured for a period of time and subsequently produce the ECM. In some embodiments, the ECM is added to the scaffold and ECM-generating cells are subsequently added. The tissue composition may feature live ECM-generating cells, dead ECM-generating cells, or a combination thereof. The ECM and/or ECM-generating cells fill in a portion of the pores in the scaffold.

The tissue composition may feature seeded cells. The seeded cells may be cultured for a period of time before use. In some embodiments, the seeded cells are not cultured for a period of time before use. The ECM-generating cells may be cultured for a period of time before seeding of the seeded cells. In some embodiments, the seeded cells are cultured to differentiate the cells, e.g., growth factors or differentiation factors may be added in culture. In some embodiments the seeded cells (or ECM-generating cells) are cultured to proliferate the cells, e.g., particular growth factors may be added in culture.

In some embodiments, the methods feature seeding the ECM-generating cells and/or seeding seeded cells. This may comprise applying the cells (e.g., ECM-generating cells, seeded cells) to the scaffold and centrifuging the cells and scaffold, applying the cells (e.g., ECM-generating cells, seeded cells) to the scaffold and rocking the cells and scaffold, applying the cells (e.g., ECM-generating cells, seeded cells) to the scaffold and allowing gravity to move the cells to the scaffold, applying the cells with a directional force such as in a spray, etc. The cells may be seeded in suspension, as spheroids, in the form of a cell sheet, in the form of a gel, in the form of a foam, etc. A cell sheet may be produced by seeding cells on a temperature sensitive plate, a low adhesion plate, or a plate with a composition that allows for detachment of the cells at a select time. A composition that allows for detachment may comprise coated liposomes, e.g., gold-coated liposomes, tuned liposomes, light activated liposomes, liposomes comprising RGD ligands, etc.

In some embodiments, the scaffold or ECM comprises an adherence factor to help adhere the ECM-generating cells and/or the seeded cells to the scaffold and/or ECM during seeding of the ECM-generating cells. The adherence factor may include a ligand, antibody, magnetic bead, liposome, liposome coated with a material to attract or attach the ECM-generating cells to the scaffold, or a combination thereof. In some embodiments, the adherence factor is a foam.

The present invention also provides methods for reducing the beat rate of contractile compositions, e.g., tissue compositions featuring cells such as cardiomyocytes that can contract. The methods may feature applying a drug or other composition to the tissue composition, wherein the drug or composition reduces the beat rate of the tissue composition. The present invention also provides methods for lowering the metabolic rate of a tissue composition. The methods may feature applying a drug or other composition to the tissue composition, wherein the drug or composition reduces the metabolic rate of the tissue composition. In some embodiments, the drug or composition reduces the beat rate of the tissue composition thereby reducing the metabolic rate. The aforementioned methods may improve the stability of the tissue composition during transport. The methods may improve the stability and/or the longevity or viability of the tissue composition during implantation. The methods may feature changing the temperature of the tissue composition to reduce the beat rate or metabolic rate of the tissue composition.

The present invention also features methods for implanting the tissue composition in a subject in need thereof. The tissue composition may be implanted at a particular beat rate, e.g., a beat rate from 0-50 bpm, 10-50 bpm, 0-40 bpm, 50-120 bpm, 0-120 bpm, etc.

The present invention also provides methods for treating disease or conditions featuring implantation of a tissue composition of the present invention in a subject in need thereof.

The present invention also provides tissue compositions produced by any of the methods described herein.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

This patent application contains at least one drawing executed in color. Copies of this patent or patent application publication with color drawing(s) will be provided by the Office upon request and payment of the necessary fee. The features and advantages of the present invention will become apparent from a consideration of the following detailed description presented in connection with the accompanying drawings in which:

FIG. 1 shows non-limiting examples of components that make up the three-dimensional tissue compositions herein.

FIG. 2 shows non-limiting examples of features of the scaffolds that may be used in the three-dimensional tissue compositions herein.

FIG. 4 also shows changes in morphology of human neonatal dermal fibroblasts (HDF) over time. At 17 days, there is a longer spindle shaped morphology of the HDF. By 28 days, there is a more homogenous population of cells that do not display the spindle shaped morphology but instead a small pebbled morphology. The present invention is not limited to the timeframe of morphological changes described in FIG. 4. For example, the long spindle shaped morphology may form at a time less than 17 days, e.g., 14 days or less, 10 days or less, 8 days or less, 5 days or less, etc., and the small pebbled morphology may form at a time less than 28 days, e.g., 24 days or less, 20 days or less, 18 days or less, 16 days or less, 14 days or less, 12 days or less, 10 days or less, etc. The time it takes for the morphological changes to occur can depend on the manufacturing method.

FIG. 6 shows non-limiting examples of features of seeded cells (which may include a single population of cells or a combination of populations of cells) that may be used in the three-dimensional tissue compositions herein.

TERMS

Figure 3A:
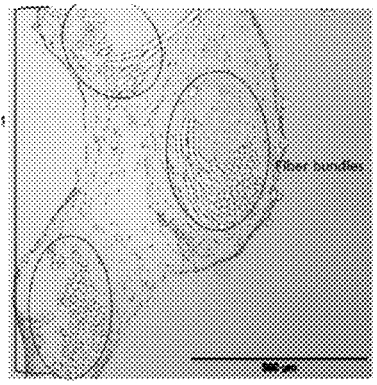
FIG. 3A shows cells and extracellular matrix (ECM) between and surrounding fiber bundles. The image is a cross-section through the tissue composition. The fiber bundles provide support for attachment and growth of proliferative cells. The proliferative cells, in this case, fibroblasts, proliferate and produce ECM to fill the pores and provide additional support structure for the attachment and growth of additional cell types across the pores. This can result in a functional tissue.

Unless otherwise explained, all technical and scientific terms used herein have the same meaning as commonly understood by one of ordinary skill in the art to which a disclosed invention belongs. The singular terms "a," "an," and "the" include plural referents unless context clearly indicates otherwise. Similarly, the word "or" is intended to include "and" unless the context clearly indicates otherwise. The term "comprising" means that other elements can also be present in addition to the defined elements presented. The use of "comprising" indicates inclusion rather than limitation. Stated another way, the term "comprising" means "including principally, but not necessary solely". Furthermore, variation of the word "comprising", such as "comprise" and "comprises", have correspondingly the same meanings. In one respect, the technology described herein related to the herein described compositions, methods, and respective component(s) thereof, as essential to the invention, yet open to the inclusion of unspecified elements, essential or not ("comprising").

All embodiments disclosed herein can be combined with other embodiments unless the context clearly dictates otherwise.

Suitable methods and materials for the practice and/or testing of embodiments of the disclosure are described below. Such methods and materials are illustrative only and are not intended to be limiting. Other methods and materials similar or equivalent to those described herein can be used. For example, conventional methods well known in the art to which the disclosure pertains are described in various general and more specific references, including, for example, Sambrook et al., *Molecular Cloning; A Laboratory Manual*, 2d ed., Cold Spring Harbor Laboratory Press, 1989; Sambrook eat al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999, *Gene Expression Technology* (Methods in Enzymology, Vol. 185, edited by D. Goeddel, 1991. Academic Press, San Diego, Calif.), "Guide to Protein Purification" in *Methods in Enzymology* (M. P. Deutshcer, ed., (1990) Academic Press, Inc.); *PCR Protocols: A Guide to Methods and Applications* (Innis, et al. 1990. Academic Press, San Diego, Calif.), *Culture of Animal Cells: A Manual of Basic Technique*, $2^{nd}$ Ed. (R. I. Freshney. 1987. Liss, Inc. New York, N.Y.), *Gene Transfer and Expression Protocols*, pp. 109-128, ed. E. J. Murray, The Humana Press Inc., Clifton, N.J.), and the Ambion 1998 Catalog (Ambion, Austin, Tex.), the disclosures of which are incorporated in their entirety herein by reference.

All publications, patent applications, patents, and other references mentioned herein are incorporated by reference in their entirety for all purposes. In case of conflict, the present specification, including explanations of terms, will control.

Although methods and materials similar or equivalent to those described herein can be used to practice or test the disclosed technology, suitable methods and materials are described below. The materials, methods, and examples are illustrative only and not intended to be limiting.

In order to facilitate review of the various embodiments of the disclosure, the following explanations of specific terms are provided:

The term "progenitor cell" refers to cells that have a cellular phenotype that is more primitive (e.g., is at an earlier step along a developmental pathway or progression than is a fully differentiated cell) relative to a cell to which it can give rise to by differentiation. Often, progenitor cells also have significant or very high proliferative potential. Progenitor cells can give rise to multiple distinct differentiated cell types or to a single differentiated cell type, depending on the developmental pathway and on the environment in which the cells develop and differentiate.

The term "stem cell" as used herein, refers to an undifferentiated cell that is capable of proliferation and giving rise to more progenitor cells having the ability to generate a large number of mother cells that can in turn give rise to differentiated, or differentiable daughter cells. The daughter cells themselves can be induced to proliferate and produce progeny that subsequently differentiate into one or more mature cell types, while also retaining one or more cells with parental developmental potential. The term "stem cell" refers to a subset of progenitors that have the capacity or potential, under particular circumstances, to differentiate to a more specialized or differentiated phenotype, and which retains the capacity, under certain circumstances, to proliferate without substantially differentiating. In one embodiment, the term stem cell refers generally to a naturally occurring mother cell whose descendants (progeny) specialize, often in different directions, by differentiation, e.g., by acquiring completely individual characters, as occurs in progressive diversification of embryonic cells and tissues. Cellular differentiation is a process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. In many biological instances, stem cells are also "multipotent" because they can produce progeny of more than one distinct cell type, but this is not required for "stem-ness." Self-renewal is the other classical part of the stem cell definition, and it is essential as used in this document. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only.

The term "embryonic stem cell" is used to refer to the pluripotent stem cells of the inner cell mass of the embryonic blastocyst (see U.S. Pat. Nos. 5,843,780, 6,200,806, which are incorporated herein by reference). Such cells can similarly be obtained from the inner cell mass of blastocysts derived from somatic cell nuclear transfer (see, for example, U.S. Pat. Nos. 5,945,577, 5,994,619, 6,235,970, which are incorporated herein by reference). The distinguishing characteristics of an embryonic stem cell define an embryonic stem cell phenotype. Accordingly, a cell has the phenotype of an embryonic stem cell if it possesses one or more of the unique characteristics of an embryonic stem cell such that that cell can be distinguished from other cells. Exemplary distinguishing embryonic stem cell characteristics include, without limitation, gene expression profile, proliferative capacity, differentiation capacity, karyotype, responsiveness to particular culture conditions, and the like.

The term "adult stem cell" or "ASC" is used to refer to any multipotent stem cell derived from non-embryonic tissue, including fetal, juvenile, and adult tissue. Stem cells have been isolated from a wide variety of adult tissues including blood, bone marrow, brain, olfactory epithelium, skin, pancreas, skeletal muscle, and cardiac muscle. Each of these stem cells can be characterized based on gene expression, factor responsiveness, and morphology in culture. As indicated above, stem cells have been found resident in virtually every tissue. Accordingly, the technology described herein appreciates that stem cell populations can be isolated from virtually any animal tissue.

As used herein, the terms "iPS cell" or "induced pluripotent stem cell" refer to a pluripotent cell artificially derived (e.g., induced by complete or partial reversal) from a differentiated somatic cell (from a non-pluripotent cell). A pluripotent cell can differentiate to cells of all three developmental germ layers.

The term "derived from" as applied to a cell being "derived from" another cell or from a tissue means the cell was either isolated from the tissue referred to, or was differentiated from the reference tissue or cell type. Thus, a cell "derived from" a particular individual's tissue was isolated from or differentiated from that individual's tissue. An individual can include an individual having a given condition. An induced pluripotent stem cell is derived from a somatic tissue of an individual, e.g., a post-partum human individual, frequently an adult. Similarly, and embryonic stem cell is derived from an embryo. A cell derived from an iPS cell refers to a cell that has differentiated from an iPS cell. Alternatively, a cell can be converted from one cell type to a different cell type by a process referred to as transdifferention or direct reprogramming. Alternatively, in the terms of iPS cells, a cell (e.g. an iPS cell) can be derived from a differentiated cell by a process referred to in the art as dedifferentiation or reprogramming.

The term "pluripotent" as used herein refers to a cell that can give rise to any type of cell in the body except germ line cells. The term "pluripotency" or a "pluripotent state" as used herein refers to a cell with the ability to differentiate into all three embryonic germ layers: endoderm (gut tissue), mesoderm (including blood, muscle, and vessels), and ectoderm (such as skin and nerve), and typically has the potential to divide in vitro for a long period of time, e.g., greater than one year or more than 30 passages. Pluripotency is also evidenced by the expression of embryonic stem (ES) cell markers, although the preferred test for pluripotency is the demonstration of the capacity to differentiate into cells of all three germ layers, as detected using, for example, a nude mouse teratoma formation assay. iPS cells are pluripotent cells. Pluripotent cells undergo further differentiation into multipotent cells that are committed to give rise to cells that have a particular function. For example, multipotent cardiovascular stem cells give rise to the cells of the heart, including cardiomyocytes, as well as other cells involved in the vasculature of the heart. Cell useful for in vitro differentiation to myocytes or cardiomyocytes as disclosed herein include, for example, iPS cells as well as multipotent cardiovascular stem cells. A major benefit of the use of iPSC or other stem cells to generate myocytes or cardiomyocytes for the compositions and methods as disclosed herein is the ability to prepare large numbers of such cells and propagate them, e.g., from a specific human patient or subject. This is in contrast to methods, compositions that rely upon the isolation and use of adult cardiac cells.

The term "differentiation" as referred to herein refers to the process whereby a cell moves further down the developmental pathway and begins expressing markers and phenotypic characteristics known to be associated with a cell that are more specialized and closer to becoming terminally differentiated cells. The pathway along which cells progress from a less committed cell to a cell that is increasingly committed to a particular cell type, and eventually to a terminally differentiated cell is referred to as progressive differentiation or progressive commitment. Cell that are more specialized (e.g., have begun to progress along a path of progressive differentiation) but not yet terminally differentiated are referred to as partially differentiated. Differentiation is a developmental process whereby cells assume a more specialized phenotype, e.g., acquire one or more characteristics or functions distinct from other cell types. In some cases, the differentiated phenotype refers to a cell phenotype that is at the mature endpoint in some developmental pathway (a so called terminally differentiated cell). In many, but not all tissues, the process of differentiation is coupled with exit from the cell cycle. In these cases, the terminally differentiated cells lose or greatly restrict their capacity to proliferate. However, in the context of this specification, the terms "differentiation" or "differentiated" refer to cells that are more specialized in their fate or function than at one time in their development. For example in the context of this application, a differentiated cell includes a ventricular cardiomyocyte which has differentiated from cardiovascular progenitor cell, where such cardiovascular progenitor cell can in some instances be derived from the differentiation of an ES cell, or alternatively from the differentiation of an induced pluripotent stem (iPS) cell, or in some embodiments from a human ES cell line. Thus, while such a ventricular cardiomyocyte cell is more specialized than the time in which it had the phenotype of a cardiovascular progenitor cell, it can also be less specialized as compared to when the cell existed as a mature cell from which the iPS cell was derived (e.g. prior to the reprogramming of the cell to form the iPS cell).

A cell that is "differentiated" relative to a progenitor cell has one or more phenotypic differences relative to that progenitor cell and characteristic of a more mature or specialized cell type. Phenotypic differences include, but are not limited to morphologic differences and differences in gene expression and biological activity, including not only the presence or absence of an expressed marker, but also differences in the amount of a marker and differences in the co-expression patterns of a set of markers.

As used herein, "proliferating" and "proliferation" refers to an increase in the number of cells in a population (growth) by means of cell division. Cell proliferation is generally understood to result from the coordinated activation of multiple signal transduction pathways in response to the environment, including growth factors and other mitogens. Cell proliferation may also be promoted by release from the actions of intra- or extracellular signals and mechanisms that block or negatively affect cell proliferation.

The term "tissue" refers to a group or layer of similarly specialized cells that together perform certain special functions.

As used herein, the phrase "cardiovascular condition, disease or disorder" is intended to include all disorders characterized by insufficient, undesired or abnormal cardiac function, e.g., arrhythmia, ischemic heart disease, hypertensive heart disease and pulmonary hypertensive heart disease, valvular disease, congenital heart disease and any condition which leads to congestive heart failure in a subject, particularly a human subject. Insufficient or abnormal cardiac function can be the result of disease, injury and/or aging. By way of background, a response to myocardial injury follows a well-defined path in which some cells die while others enter a state of hibernation where they are not yet dead but are dysfunctional. This is followed by infiltration of inflammatory cells, deposition of collagen as part of scarring, all of which happen in parallel with in-growth of new blood vessels and a degree of continued cell death. As used herein, the term "ischemia" refers to any localized tissue ischemia due to reduction of the inflow of blood. The term "myocardial ischemia" refers to circulatory disturbances caused by coronary atherosclerosis and/or inadequate oxygen supply to the myocardium. For example, an acute myocardial infarction represents an irreversible ischemic insult to myocardial tissue. This insult results in an occlusive (e.g., thrombotic or embolic) event in the coronary circulation and produces an environment in which the myocardial metabolic demands exceed the supply of oxygen to the myocardial tissue.

The term "disease" or "disorder" refers to any alteration in state of the body or of some of the organs, interrupting or disturbing the performance of their functions and/or causing symptoms such as discomfort, dysfunction, distress, or even death to the person afflicted or those in contact with a person. A disease or disorder can also related to a distemper, ailing, ailment, malady, disorder, sickness, illness, complaint, indisposition or affliction.

As used herein, the terms "treat" or "treatment" or "treating" refers to both therapeutic treatment and prophylactic or preventative measures, wherein the object is to prevent or slow the development of the disease, such as slow down the development of a cardiac disorder, or reducing at least one adverse effect or symptom of a cardiovascular condition, disease or disorder, e.g., any disorder characterized by insufficient or undesired cardiac function. Adverse effects or symptoms of cardiac disorders are well-known in the art and include, but are not limited to, dyspnea, chest pain, palpitations, dizziness, syncope, edema, cyanosis, pallor, fatigue and death. Treatment is generally "effective" if one or more symptoms or clinical markers are reduced as that term is defined herein. Alternatively, a treatment is "effective" if the progression of a disease is reduced or halted. That is, "treatment" includes not just the improvement of symptoms or decrease of markers of the disease, but also a cessation or slowing of progress or worsening of a symptom that would be expected in absence of treatment. Beneficial or desired clinical results include, but are not limited to, alleviation of one or more symptom(s), diminishment of extent of disease, stabilized (e.g., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already diagnosed with a cardiac condition, as well as those likely to develop a cardiac condition due to genetic susceptibility or other factors such as weight, diet and health.

The term "scaffold" refers to a support structure for cells and/or cellular material. The support structure may feature fibers and pores, but the scaffold is not limited to such compositions. For example, the scaffold may be in the form of a film, sponge, or solution. The scaffold may be constructed from a variety of materials such as fibers, peptides (e.g., recombinant peptides), lipids, carbohydrates, etc.

Detailed Description of the Invention

The present invention features engineered tissue compositions, e.g., three-dimensional tissue compositions that support cell growth and/or maintenance and/or differentiation, etc. The tissue compositions herein may be used for a variety of purposes including in vitro applications and in vivo applications, e.g., surgical implantation for the purpose of treating a disease or condition, research and testing, etc. The tissue compositions herein may be designed to withstand short-term or long-term storage (e.g., cryopreservation), transport. In certain embodiments, the tissue compositions can withstand certain lengths of time at room temperature.

Briefly, the engineered tissue compositions of the present invention comprise a scaffold and extracellular matrix (ECM) material. The ECM material may be generated by an ECM-generating cell type such as but not limited to fibroblasts, any other appropriate ECM-generating cell type or a combination of ECM-generating cell types. The ECM material may be produced prior to application to the scaffold or the ECM material may be produced directly on the scaffold (or a portion is pre-made and a portion is produced direction on the scaffold). In certain embodiments, the ECM material is cell-free or comprises cells (e.g., live cells, dead cells, a combination thereof). In certain embodiments, the ECM material features biologically-derived material, synthetically-derived material, or a combination thereof. In certain embodiments, the tissue composition further comprises ECM-generating cells, non-ECM generating cells, and/or additional seeded cells, e.g., cells derived from a particular tissue of interest, stem cells, etc. In certain embodiments, the tissue composition further comprises additional factors such as growth factors, drugs, or components that enhance adherence of cells to the ECM, etc.

FIG. 1 shows non-limiting examples of components that make up the tissue compositions of the present invention. For example, in certain embodiments, the tissue composition comprises a scaffold and ECM material (the ECM being cell-free, e.g., no cells are present). In some embodiments, the ECM material comprises dead cells, e.g., one living cells. In some embodiments, the ECM material is a bi-product of living cells (currently living cells, dead cells, a combination thereof, etc.). In certain embodiments, the tissue composition comprises a scaffold, ECM material, and a population of cells that are ECM-generating cells, non-ECM-generating cells, or a combination thereof. In certain embodiments, the tissue composition comprises a scaffold, ECM material, and a population of seeded cells (e.g., a cell type of interest). In certain embodiments, the tissue composition comprises a scaffold, ECM material, a population of cells that are ECM-generating cells, non-ECM-generating cells, or a combination thereof, and a population of seeded cells (e.g., a cell type of interest). The aforementioned examples of tissue compositions may comprise additional factors such as growth factors, drugs, compositions for enhancing adherence of cells, etc.

Scaffold

The scaffold used for the engineered tissue compositions herein may be constructed from a variety of types of materials, a variety of sizes of materials, a variety of configurations, etc. In certain embodiments, the scaffold comprises a plurality of fibers, wherein the fibers are arranged (e.g., woven) together yielding a plurality of pores disposed therein between. The scaffold is not limited to a fiber configuration. In certain embodiments, the scaffold comprises a film, a sponge, a gel, a solution, etc. A non-limiting example of an alternative scaffold is a sponge or film constructed from polymers, proteins, recombinant peptides, e.g., Human Collagen Type I. Sponges and films are further described below.

For embodiments with scaffolds in a fiber configuration, the fibers of the scaffold may be generally uniform in diameter or the fibers may be of various diameters. For example, in some embodiments, the scaffold comprises fibers of a first fiber type and fibers of a second fiber type, wherein the first fiber type has a diameter different from that of the second fiber type. Note the scaffold may comprise more than a first fiber type and a second fiber type, e.g., the scaffold may comprise a first fiber type and second fiber type and a third fiber type, or further a fourth fiber type, or further a fifth fiber type, etc. Scaffolds with more than one fiber type may be arranged in a variety of configurations including but not limited to a printed or spun fiber or knit or weave that has a fixed pattern of fiber type arrangement, a printed or spun fiber or knit or weave that has a random fiber type arrangement, etc. In some embodiments, small fibers extend from one or more large fibers. In some embodiments, the fibers are loosely printed or spun or knitted or woven such that space exists for cells to position therein between. The fibers may be arranged in a configuration and/or orientation that allows for a particular cell alignment.

As previously discussed, the fibers of the scaffold may be arranged in a weave or knit configuration. Weave or knit configurations may include but are not limited to a plain weave, a twilled weave, an alternating twilled weave, a knitted weave a plain Dutch weave, a Dutch twilled weave, a reverse Dutch weave, a hexagonal open worked stitch weave, a warp knit, or a combination thereof. For construction purposes, the scaffold may be weaved, knit, spun, extruded, or printed. In some embodiments, the scaffold has a ring-like configuration.

Fiber diameters may be of various sizes. For example, in some embodiments, at least a portion of the fibers have a diameter that is from 5 um to 100 um, from 10 um to 500 um, from 100 um to 1 mm (e.g., fiber bundles), etc. The present invention is not limited to the aforementioned fiber diameters.

In some embodiments, the fibers are all constructed from a single material. In some embodiments, a portion of the fibers is constructed from a first material and a portion of the fibers is constructed from a second material different from the first material. In some embodiments, a portion of the fibers is constructed from a first material, a portion of the fibers is constructed from a second material different from the first material, and a portion of the fibers is constructed from a third material different from the first and second materials. The present invention is not limited to three different material types; the scaffold may be constructed from four different materials, five, six, etc. In some embodiments, one or more fibers of the scaffold are constructed from two or more materials, e.g., individual fibers are made from a combination of materials.

Materials used for constructing the scaffold (e.g., a scaffold with fibers and/or other components such as peptides) may include but are not limited to polyglycolide, polylactide, polyhydroxobutyrate, poly(anhydrides), poly(dioxanone), poly (trimethylene carbonate), polyglactin, poly (lactic acid), polyvinylidene fluoride, polyesters, silicone, polyurethane, polymethylmethacrylate, polypropylene, polyethylene, poliglecaprone-25 monofilament, a polycarbonate, a polyamide, a polyesters, a polystyrene, a polyacrylate, a polyvinyl, polytetrafluorethylene, thermanox, nitrocellulose, collagen, fibrin, elastin, silk, metals, TMC, polyester, gelatin, dextran, proteins, peptides, or a combination thereof. For example, in some embodiments, the first material comprises at least glycolide, lactide and trimethylene carbonate, and the second material comprises at least lactide and trimethylene carbonate.

As previously discussed, in certain embodiments, the scaffold is in the form of a film. In certain embodiments, the scaffold is in solution. In certain embodiments, the scaffold is a sponge. Regarding the sponge configuration, in some embodiments, the sponge has a generally uniform diameter. In certain embodiments, the sponge has a non-uniform diameter. In certain embodiments, the sponge is stratified having multiple levels or layers (e.g., a lower level, an upper level, etc.), wherein one layer may have a first uniformity and a different layer may have a second uniformity. The sponge may feature grooves or ridges. For example, one layer, e.g., a top level or a bottom layer, may feature ridges or grooves.

The scaffold may be constructed from a variety of materials including but not limited to peptides (e.g., recombinant peptides), carbohydrates, lipids, etc. In certain embodiments, the scaffold comprises both recombinant peptides and fibers (e.g., absorbable/degradable fibers, non-absorbable/degradable fibers, or a combination thereof). A non-limiting example of a recombinant peptide used for creating a film scaffold or sponge scaffold or solution scaffold includes collagen type I.

The scaffold may be constructed from biologically-derived material, synthetically-derived material, or a combination of synthetically-derived and biologically-derived material.

The scaffold may feature grooves and ridges, e.g., parallel grooves and ridges, organized or patterned grooves and ridges, randomly organized grooves and ridges. The configuration of the scaffold may help enhance proliferation or differentiation/maturation of a cell. The configuration of the scaffold may help organize the cells in a particular direction or orientation, e.g., align the cells for a particular purpose such as muscle contraction.

The scaffold may be constructed in a variety of thicknesses. For example, in some embodiments, the scaffold is at least 25 um thick. In some embodiments, the scaffold is at least 40 um thick. In some embodiments, the scaffold is at least 50 um thick. In some embodiments, the scaffold is at least 100 um thick. In some embodiments, the scaffold is at least 250 um thick. In some embodiments, the scaffold is at least 500 um thick. In some embodiments, the scaffold is at least 1 mm thick. In some embodiments, the scaffold is at least 2 mm thick. In some embodiments, the scaffold is from 30 or 40 um to 820 or 850 um. In some embodiments, the scaffold is from 50 um to 500 um thick. In some embodiments, the scaffold is from 500 um to 1 mm thick. In some embodiments, the scaffold is from 1 mm to 2 mm thick. The present invention is not limited to the aforementioned thicknesses, e.g., 2 to 3 mm, 3 to 4 mm, 4 to 5 mm, 5 to 6 mm, etc. For example, the thickness may be from 45 um to 1070 um, 45 to 499 um, 246 to 1070 um, etc. The aforementioned thicknesses may apply to the engineered tissue composition (e.g., the scaffold with ECM optionally with cells, etc.). For example, in certain embodiments, the engineered tissue composition is from 200-1000 microns in thickness.

Some components (or all of the components) of the scaffold, e.g., fibers, peptides, etc. may be resorbable, absorbable, or degradable. For example, one or more of the components may resorb/absorb/degrade/dissolve as proliferative ECM-generating cells replicate on and in the scaffold. In an example wherein the scaffold comprises two or more different fiber types, in certain embodiments, fibers of a first fiber type may be resorbable/absorbable/degradable and fibers of a second fiber type may not be resorbable/absorbable/degradable. In certain embodiments, all of the scaffold components may be resorbable/absorbable/degradable in some capacity, e.g., a first fiber type may be resorbable/absorbable/degradable at a rate that is different than that of a second fiber type. The scaffold may feature a degradation profile (timed, tiered), wherein portions of the scaffold degrade at particular times. Any appropriate degradable materials or combinations thereof may achieve a desired degradation profile.

For the examples below, the degradation profile (when the scaffold resorbs/absorbs/degrades) is measured starting from the time of surgical implantation of the tissue composition. In some embodiments, a portion or all of the scaffold resorbs/absorbs/degrades within 1 day, within 2 days, within 3 days, within 4 days, within 5 days, within 6 days, within 1 week, within 8 days, within 9 days, within 10 days, within 11 days, within 12 days, within 13 days, within 2 weeks, within 3 weeks, within 1 month, within 2 months, within 3 months, within 4 months, within 5 months, within 6 months, within 1 year, within 2 years, within 3 years, within 4 years, within 5 years, etc. In certain embodiments the scaffold does not fully resorb/absorb/degrade (the scaffold is non-absorbable).

The mechanical properties (e.g., stiffness, etc.) of the scaffold may change as components (e.g., fibers and/or other materials such as peptides) of the scaffold resorb/absorb/degrade.

Without wishing to limit the present invention to any theory or mechanism, it is believed that a scaffold that does not significantly curl up or fold over on itself during surgical implantation may provide advantages, e.g., the tissue composition may be easier for the surgeons to implant if it does not fold over on itself.

FIG. 2 shows non-limiting examples of features of the scaffold used in the tissue compositions of the present invention. For example, as previously discussed, in certain embodiments the scaffold comprises absorbable/degradable fibers, non-absorbable/degradable fibers, or a combination thereof. In certain embodiments, the scaffold comprises a sponge (e.g., constructed with recombinant peptides, e.g., Human Collagen Type I). In some embodiments, the scaffold comprises a film (e.g., constructed with recombinant peptides, e.g., Human Collagen Type I). In some embodiments, the scaffold is in solution. In certain embodiments, the scaffold comprises both recombinant peptides (forming a film or sponge) and fibers (e.g., absorbable/degradable fibers, non-absorbable/degradable fibers, or a combination thereof). In certain embodiments, the scaffold comprises biologically-derived components (e.g., naturally produced by cells), synthetically-derived components, or a combination thereof. In certain embodiments, the scaffold comprises additional features or properties that enhances the adherence of cells and/or ECM. For example, in certain embodiments, the scaffold has a hydrophilicity adapted to allow adherence of cells and/or ECM. In certain embodiments, the scaffold has a surface roughness adapted to allow adherence of cells and/or ECM. Non-limiting examples of compositions or features that may enhance cell adherence may include certain textures or roughness, certain hydrophilic compounds or features, certain ligands, RGD-coated materials, etc.

Mechanical Properties of Scaffold

The scaffold may be anisotropic, e.g., the mechanical properties of the scaffold may be different in one direction than the other. Or, the scaffold may be isotropic. The scaffold has a variety of mechanical properties related to strength and flexibility.

There is generally a difference between the base material properties (e.g., the scaffold alone) and the properties of the tissue composition (with the fibroblasts and ECM). For example, if the scaffold features components (e.g., fibers and/or peptides) that are degradable (e.g., fibers or peptides that degrade during culture), the scaffold may be stiffer than what is ultimately used as the tissue composition (e.g., for in vive use). In some embodiments, a scaffold may be chosen with a material in the GPa range, but when the tissue composition is implanted, it may be in the MPa range, likewise, a scaffold may be chosen in the MPa range but when the tissue composition is implanted it may be in the kPa range. In some embodiments, the implanted materials (the property of the tissue composition) may be below 100 MPa.

The elastic modulus (stiffness) may be from 20 kPa to 100 GPa. The scaffold may have a burst strength from 20 N/cm to 200 N/cm, from 50 N/cm to 100 N/cm, from 75 N/cm to 90 N/cm, etc. The scaffold may have a parallel/perpendicular tear resistance from 10N/5N to 50N/40N. The scaffold may have a parallel/perpendicular tear resistance from 30/31N to 350N/36N. In some embodiments, the scaffold has a longitudinal stiffness from 1 N/mm to 50 N/mm. In some embodiments, the scaffold has a longitudinal stiffness from 4 N/mm to 30 N/mm. In some embodiments, the scaffold has a transverse stiffness from 0.5 N/mm to 5 N/mm. In some embodiments, the scaffold has a longitudinal stiffness that is different from a transverse stiffness. In some embodiments, the scaffold has a longitudinal stiffness that is the same as a transverse stiffness. In some embodiments, the scaffold has a longitudinal maximum force from 10 kPa to 100 MPa. In some embodiments, the scaffold has a transverse maximum force from 10 kPa to 100 MPa. In some embodiments, the scaffold has a stiffness from 5 to 3000 kPa. In some embodiments, the scaffold has a stiffness from 3000 to 4600 kPa. In some embodiments, the scaffold has a stiffness greater than 4600 kPa. The scaffold may feature fibers with different stiffness e.g., fibers with stiffness of 1-20 MPa and fibers with stiffness >10 Mpa. As previously discussed, the stiffness of the scaffold prior to culturing of cells may be different from the end product, e.g., the tissue composition.

In some embodiments, the tissue composition (e.g., end product) may be from 20 kPa to 50 MPa, however the present invention is not limited to those values.

The mechanical properties (e.g., stiffness, etc.) may change over the course of manufacturing, cell proliferation, cell differentiation, implantation, etc. The present invention is not limited to the mechanical property parameters described herein.

In certain embodiments, the engineered tissue composition allows for electrical signal transduction.

Scaffold Pores

The density of pores, e.g., number of pores per unit of area (e.g., number of pores per mm$^2$ of scaffold), may help cells to efficiently grow across the scaffold. In some embodiments, the pores are closely spaced and/or pores are positioned above pores slightly overlapping; however, the present invention is not limited to closely spaced pores or pores positioned above pores slightly overlapping. Further, the density of pores may depend on the type of material used for the scaffold, the thickness of the scaffold, the type of weave of the scaffold, etc. In some embodiments, the scaffold has from 1 to 1,000 pores per cm$^2$. In some embodiments, the scaffold has from 10 to 1,000 pores per cm$^2$. In some embodiments, the scaffold has from 100 to 1,000 pores per cm$^2$. In some embodiments, the scaffold has from 100 to 1,000 pores per mm$^2$. In some embodiments, the scaffold has from 100 to 500 pores per mm$^2$. In some embodiments, the scaffold has from 200 to 1,000 pores per mm$^2$. The pore density may also change over time. For example, in some embodiments, components of the scaffold (e.g., fibers and/or peptides, etc.) may degrade (e.g., biodegrade, resorb, absorb, etc.), yielding a different pore density than what was originally present in the scaffold.

In some embodiments, the pores are arranged uniformly throughout the scaffold. In some embodiments, the pores are arranged randomly throughout the scaffold. In some embodiments, the pores are arranged in a pattern throughout the scaffold. The pores may be of various shapes (e.g., cross-sectional shapes), e.g., rectangular, rounded rectangular, or of other geometric shape or irregular shape or shape combination including but not limited to hexagonal, circular, oval, figure eight-shaped, etc. Thus, the pores may be described as having a height, width, length, diameter, area, etc. In some embodiments, the pores (e.g., one or more of the pores) of the scaffold have an area from 0.1 µm$^2$ to 100 µm$^2$, from 1 µm$^2$ to 1000 µm$^2$, from 100 µm$^2$ to 5000 µm$^2$, from 0.1 µm$^2$ to 0.01 mm$^2$, from 0.1 µm$^2$ to 0.1 mm$^2$, from 0.1 µm$^2$ to 1 mm$^2$, from 0.1 µm$^2$ to 2 mm$^2$, from 0.1 µm$^2$ to 10 mm$^2$, etc. In some embodiments, the average pores size is approximately 104,540 µm$^2$. In some embodiments, the average pore size is from 5,000 µm$^2$ to over 1,000,000 µm$^2$. In some embodiments, the pores have a diameter that is from 50 µm to 90 µm. In some embodiments, the pores have a diameter from 50 µm to 200 µm. In some embodiments, the pores have a diameter from 200 µm to 400 µm, 200 µm to 500 µm, etc. In some embodiments, the pores have a diameter from 500 µm to 1000 µm. In some embodiments, the pores have a diameter from 500 µm to 1500 µm. In some embodiments, the pores have a diameter from 800 µm to 1200 µm. In some embodiments, the pores have a diameter from 800 µm to 1000 µm.

In some embodiments, the scaffold retains at least 50% of its mechanical strength for at least 4 weeks, at least 5 weeks, at least 8 weeks, at least 10 weeks, at least 15 weeks, at least 20 weeks, at least 30 weeks, at least 40 weeks, etc.

In some embodiments, the scaffold degrades in no less than 3 weeks. In some embodiments, the scaffold degrades in no less than 4 weeks after implantation. In some embodiments, the scaffold degrades in no less than 6 weeks after implantation. In some embodiments, the scaffold degrades in no less than 8 weeks after implantation. In some embodiments, the scaffold degrades in no less than 10 weeks after implantation.

The scaffold may feature two different fibers, wherein one is fast resorbing and one is slow resorbing (relative to each other), to allow for dual-stage resorption.

Extracellular Matrix Material

As previously discussed, the engineered tissue compositions of the present invention comprise extracellular matrix (ECM) material. The ECM may be produced by ECM-generating cells, however the present invention is not limited to ECM produced by ECM-generating cells. In certain embodiments, the ECM comprises only synthetically-derived material. In certain embodiments, the ECM comprises biologically-derived material (e.g., ECM produced by ECM-generating cells). In certain embodiments, the ECM comprises a combination of biologically-derived material and synthetically-derived material. As an example, materials such as synthetically-produced collagen and fibronectin (and the like, e.g., materials discussed herein) may be combined to form an ECM without the need for ECM-generating cells.

In some embodiments, from 0 to 10% of the ECM or tissue composition (by area or volume) is synthetically-derived. In some embodiments, from 10 to 25% of the ECM or tissue composition (by area or volume) is synthetically-derived. In some embodiments, from 25 to 40% of the ECM or tissue composition (by area or volume) is synthetically-derived. In some embodiments, from 40 to 60% of the ECM or tissue composition (by area or volume) is synthetically-derived. In some embodiments, from 60 to 75% of the ECM or tissue composition (by area or volume) is synthetically-derived. In some embodiments, from 75 to 90% of the ECM or tissue composition (by area or volume) is synthetically-derived. In some embodiments, from 50 to 95% of the ECM or tissue composition (by area or volume) is synthetically-derived.

Components of the ECM may include but are not limited to collagen (e.g., collagen type I, collagen Type III), elastin, fibronectin, laminins, tenascin, proteoglycans, glycosaminoglycans (e.g., Veriscan, Decorin, Betaglycan, Syndecan), etc. (see Naughton, 2002, Ann N Y Acad Sci, 961:372-85). In some embodiments, exogenous gelatin is deposited on the scaffold. In some embodiments, exogenous collagen, fibronectin, fibrin is added (or other appropriate ECM components).

Without wishing to limit the present invention to any theory or mechanism, it is believed that a certain amount of ECM is beneficial for the engineered tissue composition to be effective (e.g., effective for accepting seed cells, for differentiating seed cells, for surgical implantation, etc.).

In certain embodiments, the ECM is produced by seeding ECM-generating cells in and/or on the scaffold (e.g., on and/or within the pores and components of the scaffold), wherein the ECM-generating cells subsequently proliferate and expand in and/or on and through the scaffold, producing ECM. The ECM-generating cells may migrate along the components (e.g., fibers, peptides, etc.) of the scaffold and further within the pores (e.g., along with ECM that is generated). The seeding process for the ECM-generating cells (and/or other cells herein) may utilize various steps to enhance adherence of the cells onto the scaffold, such as but not limited to centrifugation or other appropriate forces (e.g., electrical force), or combinations thereof.

In certain embodiments, the ECM is produced by ECM-generating cells prior to the application of the ECM onto the scaffold. As an example, following production of the ECM by the ECM-generating cells, the ECM material along with the ECM-generating cells may be applied to the scaffold. Alternatively, in certain embodiments, the ECM material produced by the ECM-generating cells may be made cell-free and subsequently applied to the scaffold. In certain embodiments, a population of cells is seeded in and/or on the scaffold prior to the application of the ECM.

Note that the ECM-generating cells may be live or dead (or a combination of live and dead cells). For example, the tissue composition may comprise the scaffold, ECM, and live ECM-generating cells (e.g., fibroblasts or other ECM-generating cell type or a combinations thereof). In certain embodiments, the tissue composition comprises the scaffold, ECM, and dead ECM-generating cells. In certain embodiments, the tissue composition comprises the scaffold, ECM, and a population of live ECM-generating cells and a population of dead ECM-generating cells.

The ECM-generating cells may be fibroblasts, e.g., human dermal fibroblasts. However, the present invention is not limited to fibroblasts. In some embodiments, the ECM-generating cells comprise fibroblasts, osteoblasts, chondrocytes, glial cells, neural stem cells, cardiomyocytes, myofibroblasts, the like, or a combination thereof. As discussed herein, in certain embodiments, the ECM-generating cells may be genetically engineered to produce specific ECM and/or growth factors and/or engineered to proliferate, etc.

The ECM-generating cells may be derived from an appropriate source or host. For example, in some embodiments, the ECM-generating cells are human cells. In some embodiments, the ECM-generating cells are primate cells. In some embodiments, the ECM-generating cells are mouse cells, rat cells, goat cells, rabbit cells, horse cells, canine, feline, or any other host-derived cells. In certain embodiments, the ECM-generating cells are genetically modified to be universal cells (non-immunogenic).

As previously discussed, the ECM-generating cells may be fibroblasts. In certain embodiments, the fibroblasts are iPSC-derived fibroblasts. In some embodiments, the fibroblasts are skin-derived fibroblasts, e.g., dermal neonatal fibroblasts. In some embodiments, the fibroblasts are blood-derived fibroblasts. In some embodiments, the fibroblasts are heart-derived, muscle-derived, liver-derived, pancreas-derived, adipose tissue-derived, central nervous system (CNS)-derived, or lung-derived fibroblasts.

In certain embodiments, the ECM-generating cells are wild type cells. In certain embodiments, the ECM-generating cells are genetically modified, e.g., engineered to express one or more genes of interest. In certain embodiments, the ECM-generating cells are a combination of wild type and genetically modified cells.

The ECM-generating cells may form a layer atop the scaffold. (In certain embodiments, the ECM cells that are seeded on/in the scaffold are already in ECM. In certain embodiments, cells in the ECM are alive and/or dead.) In some embodiments, the ECM-generating cells are disposed within and/or on top of the scaffold. The ECM-generating cells may be present in aggregates in or on top of the scaffold, form one or more layers on the scaffold, adopt an alternative arrangement within or on top of the scaffold, or a combination thereof. The tissue compositions of the present invention may have layers of cells, e.g., from 3 to 500 cell layers. The cell layers may be made up of ECM-generating cells, non-ECM generating cells, or a combination thereof.

As ECM-generating cells proliferate and produce ECM in and on the scaffold, the ECM-generating cells and/or the ECM fill in at least a portion of the pores of the scaffold. The ECM-generating cells and/or the ECM may then fill in all of the pores of the scaffold. Note in some embodiments, a cell free ECM material is used that fills in a portion or all of the area of the pores of the scaffold.

Figure 3B:
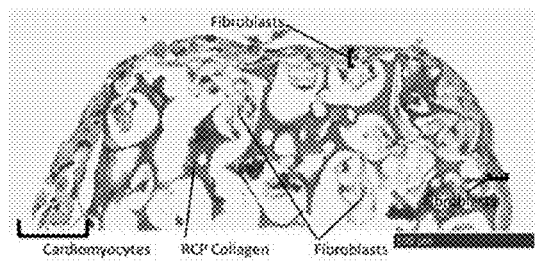
FIG. 3B shows a recombinant peptide scaffold (collagen I) infilled with human dermal fibroblasts and seeded topically with iPSC-derived cardiomyocytes. The fibroblasts penetrate the pores of the scaffold. The cardiomyocytes sit on the surface in a stratified culture.
Figure 3C:
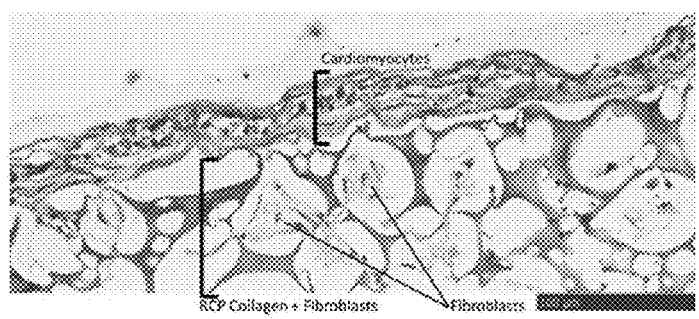
FIG. 3C shows a recombinant peptide scaffold (collagen I) infilled with human dermal fibroblasts and seeded topically with iPSC-derived cardiomyocytes. The fibroblasts penetrate the pores of the scaffold. The cardiomyocytes sit on the surface in a stratified culture.
Figure 3D:
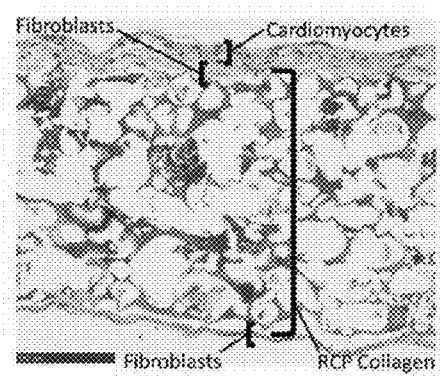
FIG. 3D shows a recombinant peptide scaffold (collagen I) (a "hollow" scaffold) topically seeded with human dermal fibroblasts. The fibroblasts do not embed the scaffold but rather form a layer of cells on the top and bottom. One side also includes iPSC-derived cardiomyocytes in a stratified culture.
Figure 3E:
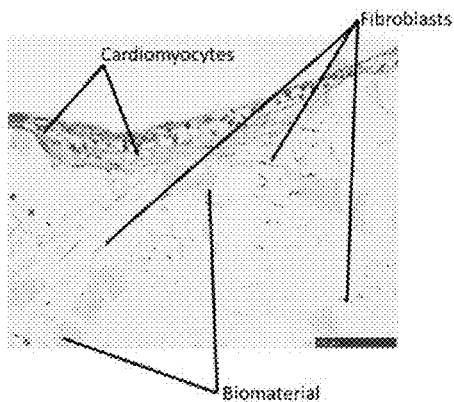
FIG. 3E shows a tissue composition (20× magnification) comprising fibroblasts and cardiomyocytes seeded on a scaffold made from polyglycolic acid (PGA) and trimethylene carbonate (TMC).
Figure 3F:
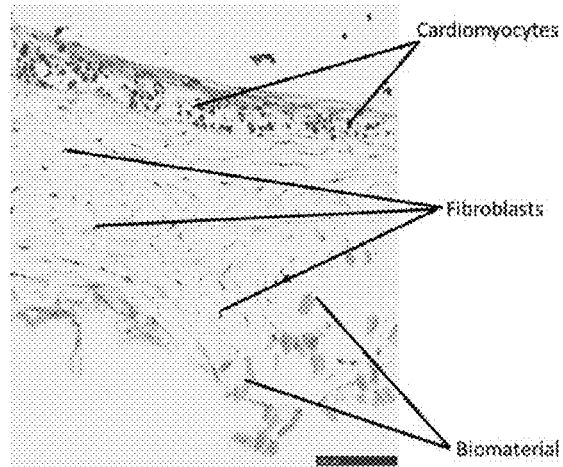
FIG. 3F shows a tissue composition (20× magnification) comprising fibroblasts and cardiomyocytes seeded on a scaffold made from polyglycolic acid (PGA).

Examples of tissue compositions of the present invention are shown in FIG. 3A, FIG. 3B, FIG. 3C, FIG. 3D, FIG. 3E, and FIG. 3F. FIG. 3A shows fibroblasts and extracellular matrix (ECM) between and surrounding fiber bundles of a particular scaffold. The fibroblasts proliferate and produce ECM to fill the pores and provide additional support structure for the attachment and growth of additional cell types across the pores. FIG. 3B and FIG. 3C show scaffolds made from recombinant peptides (collagen I) infilled with human dermal fibroblasts and seeded topically with iPSC-derived cardiomyocytes. The fibroblasts penetrate the pores of the scaffold. The cardiomyocytes sit on the surface in a stratified culture. FIG. 3D shows a scaffold made from recombinant peptides (collagen I) in a "hollow" configuration. The scaffold is topically seeded with human dermal fibroblasts. The fibroblasts do not embed the scaffold but rather form a layer of cells on the top and bottom. One side also includes iPSC-derived cardiomyocytes in a stratified culture. FIG. 3E shows a tissue composition (20× magnification) comprising fibroblasts and cardiomyocytes seeded on a scaffold made from polyglycolic acid (PGA) and trimethylene carbonate (TMC). FIG. 3F shows a tissue composition (20× magnification) comprising fibroblasts and cardiomyocytes seeded on a scaffold made from polyglycolic acid (PGA).

With respect to tissue compositions comprising scaffold made from recombinant peptides, in certain embodiments, the recombinant peptide scaffold is from 300 to 500 µm thick. In certain embodiments, the cardiomyocyte later is from 20 to 50 µm thick. In certain embodiments, the pores are from 50 to 90 µm in diameter. The present invention is not limited to the aforementioned dimensions.

In some embodiments, 100% of the area of the pores is filled by the ECM-generating cells and/or the ECM. In some embodiments, at least 99%, at least 98%, at least 97%, at least 96%, at least 95%, at least 90%, at least 85%, at least 80%, at least 75%, at least 70%, at least 50%, etc. of the area of the pores is filled by the ECM-generating cell and/or the ECM.

In some embodiments, at least 50% of the area of the pores is filled (filled by the ECM-generating cells and/or the ECM) within 2 to 10 days of seeding the ECM-generating cells, within 3 to 10 days of seeding the ECM-generating cells, within 4 to 10 days of seeding the ECM-generating cells, within 5 to 10 days of seeding the ECM-generating cells, within 8 to 10 days of seeding the ECM-generating cells, within 5 to 15 days of seeding the ECM-generating cells, within 8 to 15 days of seeding the ECM-generating cells, within 10 to 15 days of seeding the ECM-generating cells, within 12 to 15 days of seeding the ECM-generating cells, within 5 to 25 days of seeding the ECM-generating cells, within 10 to 25 days of seeding the ECM-generating cells, within 15 to 25 days of seeding the ECM-generating cells, within 20 to 25 days of seeding the ECM-generating cells, etc.

The time it takes for the pores to fill may depend on certain factors, e.g., how the cells are seeded, e.g., whether or not the tissue composition is rocked during the seeding process, rocking rates, whether centrifugation was used during the seeding process, etc. As an example, with rocking, in certain embodiments, at least 50% of the area of the pores is filled (filled by the ECM-generating cells and/or the ECM) within 5 to 10 days of seeding the ECM-generating cells, whereas in certain embodiments without rocking, at least 50% of the area of the pores is filled (filled by the ECM-generating cells and/or the ECM) within 14-17 days of seeding the ECM-generating cells. The aforementioned example is not mean to limit the present invention in any way and merely serves as an example to describe that rocking may accelerate the time needed to fill at least 50% of the area of the pores.

Figures 4, 5:
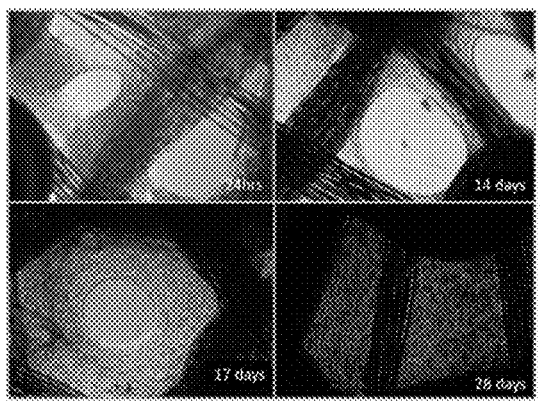
FIG. 4 shows images of a tissue composition at 24 hours (top left panel), 14 days (top right panel), 17 days (bottom left panel), and 28 days (bottom right panel). The pores fill in over time.
FIG. 5 shows non-limiting examples of features of the extracellular matrix (ECM) that is used in the three-dimensional tissue compositions herein. Note the features of the ECM may affect the stiffness of the tissue composition, the pore size, cell growth, cell orientation, etc.

As the ECM-generating cells proliferate and generate ECM in the scaffold, the cells undergo morphological changes (e.g., see FIG. 3A, FIG. 4). FIG. 4 shows images of a tissue composition over several days (1, 14, 17, and 28 days) following seeding with human neonatal dermal fibroblasts (HDF), wherein the pores fill in over time. At 17 days, there is a longer spindle shaped morphology of the HDF. By 28 days, there is a more homogenous population of cells that do not display the spindle shaped morphology but instead a small pebbled morphology. The present invention is not limited to the timeframe of morphological changes described in FIG. 4. For example, the long spindle shaped morphology may form at a time less than 17 days, e.g., in 16 days, 15 days, 14 days, 13 days, 12 days, 11 days, 10 days, 9 days, 8 days, 7 days, 6 days, 5 days, 4 days, less than 4 days, 16 days or less, 15 days or less, 14 days or less, 13 days or less, 12 days or less, 11 days or less, 10 days or less, 9 days or less, 8 days or less, 7 days or less, 6 days or less, 5 days or less, etc. In certain embodiments, the small pebbled morphology may form at a time less than 28 days, e.g., in 27 days, 26 days, 25 days, 24 days, 23 days, 22 days, 21 days, 20 days, 19 days, 18 days, 17 days, 16 days, 15 days, 14 days, 13 days, 12 days, 11 days, 10 days, 9 days, 8 days, less than 8 days, 26 days or less, 25 days or less, 24 days or less, 23 days or less, 22 days or less, 21 days or less, 20 days or less, 19 days or less, 18 days or less, 17 days or less, 16 days or less, 15 days or less, 14 days or less, 13 days or less, 12 days or less, 11 days or less, 10 days or less, 9 days or less, 8 days or less, etc. The time it takes for the morphological changes to occur can depend on the manufacturing method.

27 The engineered tissue compositions may comprise a final density of ECM-generating cells from $5 \times 10^5$ cells/cm$^2$ to $5 \times 10^6$ cells/cm$^2$. In some embodiments, the engineered tissue compositions comprise a final density of ECM-generating cells from $1 \times 10^5$ cells/cm$^2$ to $1 \times 10^7$ cells/cm$^2$. In some embodiments, the engineered tissue compositions comprise a final density of ECM-generating cells from $1 \times 10^4$ cells/cm$^2$ to $1 \times 10^8$ cells/cm$^2$. The present invention is not limited to the aforementioned final densities of ECM-generating cells.

In some embodiments, additional factors are added to the ECM, the scaffold, and/or the ECM-producing cells. Additional factors may be added to enhance the production of ECM, or for other purposes such as for enhancing cell growth, maintenance, and/or differentiation, for enhancing adherence of cells and/or ECM, etc. As a non-limiting example, ascorbic acid, which helps drive ECM deposits, may be added. In some embodiments, the additional factor is for enhancing adherence of the ECM-generating cells and/or for enhancing adherence of seeded cells.

In some embodiments, exogenous growth factors are added either along or in combination with the ECM and/or ECM-generating cells and/or the scaffold. The growth factors (e.g., those secreted by the fibroblasts, those added exogenously) may improve proliferation (of the fibroblasts themselves, of the seeded cells), seeding efficiency (of the fibroblasts themselves, of the seeded cells), integration of the fibroblasts into the scaffold, generation of the ECM, etc. Growth factors may include but are not limited to vascular endothelial growth factor (VEGF), basic fibroblast growth factor (bFGF), hepatocyte growth factor (HGF), angiopoietin-1, matrix deposit factors (e.g., Transforming growth factor (TGF-b1), Transforming growth factor (TBG-b3)), mitogenic factors (e.g., Platelet derived growth factor A (PDGF-A), Insulin like growth factor 1 (IGF-1), Erythropoietin (EPO), Heparin binding epidermal growth factor (HBEGF), Transforming growth factor a (TGFa)), angiogenic factors (e.g., Angiogenein, Angiopoientin-2), Endothelial Growth Factor, Leptin, Platelet derived growth factor BB (PDGF-BB), Vascular endothelial growth factor (VEGF), Hepatocyte growth factor (HGF), Basic Fibroblasts growth factor (bFGF), Secreted protein acid and rich in cysteine (SPARC), Interleukin 6 (IL-6). Interleukin 8 (IL-8), Inflammatory Cytokines (e.g., Interferon-gamma, Interleukin 1a, Interleukin 1b, Interleukin 6 (IL-6), Interleukin 8 (IL-8), Monocyte chemotactic protein 1, Granulocyte colony stimulating factor (GCSF), Tumor necrosis factor a (TNFa)), etc. (see Naughton, 2002, Ann N Y Acad Sci, 961:372-85; Lancaster et al., 2010, Tissue Eng Part A, 16(10):3065-73). Growth factors from other cells, e.g., therapeutic cells, may be added. For example, cardiomyocytes secrete specific factors to stimulate in vitro signaling, maturation, myokine activities and in vivo myogenesis, etc., and said growth factors may also be added exogenously or via seeding of another cell type.

In some embodiments, the scaffold makes up between 1 to 70% of the tissue composition by volume. In some embodiments, the scaffold makes up between 1 to 80% of the tissue composition by volume. In some embodiments, the scaffold makes up between 5 to 50% of the tissue composition by volume. In some embodiments, the ECM and ECM-generating cells make up at least 20% of the tissue composition by volume. In some embodiments, the ECM and ECM-generating cells make up from 20 to 50% of the tissue composition by volume. In some embodiments, the ECM and ECM-generating cells make up from 50 to 75% of the tissue composition by volume. In some embodiments, the ECM and ECM-generating cells make up from 50 to 99% of the tissue composition by volume. In some embodiments, the ECM and ECM-generating cells make up from 30 to 99% of the tissue composition by volume. The amount of the tissue composition made up of ECM and ECM-generating cells (vs. scaffold) may depend on various factors, e.g., amount of ECM-generating cells seeded at the start of culture, the expected degradation rate of scaffold material, the amount of seed cell population, etc. For example, the amount of the tissue composition made up of seed cells may range from 3 to 60% of the tissue composition.

As an example, specific tissue compositions (comprising ECM and ECM generating cells) constructed with particular scaffold materials (e.g., a dual-fiber/slower degrading scaffold, a lactide scaffold, a polyglactin scaffold) were analyzed for assessing the mass of the cells and ECM relative to scaffold mass. First the scaffold was weighed, and then the tissue composition (fully cultured HDF-scaffold composition) was weighed both wet and dry. With the dual-fiber scaffold cultured with cells and ECM, the wet weight was 0.058 g/cm2 with a dry weight of 0.028 g/cm2 whereas the dual-fiber scaffold alone had a wet weight of 0.021 g/cm2 and dry weight of 0.016 g/cm2. Thus the mass of ECM and ECM depositing cells was 0.037 g/cm2. The dry weight was 0.012 g/cm2.

The engineered tissue composition may be generally flat. The engineered tissue composition may itself have a curl, or microscopic features of the tissue composition may have convex or concave components. Without wishing to limit the present invention to any theory or mechanism, it is possible that a concave structure may be beneficial for seeding, adhesion, and integration of cells.

FIG. 5 shows non-limiting examples of features of the ECM used in the tissue compositions of the present invention. For example, as previously discussed, in certain embodiments the ECM is biologically-derived (e.g., from ECM-generating cells), synthetically-derived, or a combination thereof. In certain embodiments, the ECM-generating cells are wild type, genetically modified, or the ECM-generating cells features a population of wild type cells and a population of genetically modified cells. In certain embodiments, the ECM is cell free. In certain embodiments, the ECM comprises ECM-generating cells that are live, dead, or feature a population of live cells and a population of dead cells. In certain embodiments, the ECM comprises growth factors, drugs, and/or other compositions that help ECM production, cell adherence, ECM adherence to the scaffold, etc.

Seeded Cells

The tissue compositions of the present invention may comprise seeded cells. The seeded cells may be of any appropriate cell type (and from any appropriate host or genetically modified to be universal cells). For example, in some embodiments, the seed cells are human cells. In some embodiments, the seed cells are mouse cells, rat cells, goat cells, rabbit cells, horse cells, canine, feline, or any other host-derived cells. The seed cells may be associated with blood, cardiac tissue, skeletal muscle tissue, liver tissue, pancreatic tissue, lung tissue, bone tissue, umbilical cord tissue, endothelial tissue, central nervous system tissue, gastrointestinal tissue, endocrine cells, paracrine cells, enzyme-secreting cells, stem cells thereof, progenitors thereof, prokaryote, eukaryote or other oxygen emitting particle, or a combination thereof. Note the seeded cells may be from the same donor as the ECM-generating cells. In certain embodiments, the seeded cells are from a donor different from that of the ECM-generating cells.

The seeded cells may be proliferative, non-proliferative, or a combination thereof. The seeded cells may be stem cells (e.g., adult stem cells, embryonic stem cells, induced pluripotent stem cells), primary cells, progenitor cells, etc. For example, the seeded cells may be human inducible pluripotent stem cell-derived cells (hiPSCs), e.g., human inducible pluripotent stem cell-derived cardiomyocytes (hiPSC-CMs). The seed cells may be terminally differentiated cells, e.g., terminally differentiated cardiomyocytes, hepatocytes, beta cells, endoderm, smooth muscle cells, salivary cells, etc.

The seeded cells may be mature or immature. For example, cardiac progenitor cells may express one or more markers such as but not limited to MESP1, GATA4, ISL1, NKX2.5, the like, or a combination thereof. Nascent cardiomyocytes may express one or more markers such as but not limited to CTNT, MHC, MLC, sarcomeric actinin, the like, or a combination thereof. iPSCs may express one or more markers such as but not limited to Oct-4, LIN-23, the like, or a combination thereof.

The seeded cells may be wild type cells. In certain embodiments, the seeded cells are genetically modified to express one or more genes of interest. In certain embodiments, the seeded cells comprise a population of wild type cells and a population of genetically modified cells. For example, genes of interest may include but are not limited to thymosin beta-4 (TB4), akt murine thyoma viral oncogene homolog (AKT1), stroma cell-derived factor-1 alpha (SDF-1), hepatocyte growth factor (HGF), insulin like growth factor one (IGF-1), erythropoietin (EPO), etc. The present invention is not limited to the aforementioned genes, nor is the present invention limited to genetically modified cells that express a gene for a particular therapeutic purpose. In some embodiments, included with the seeded cells may be additional cells or particles such as prokaryotes, eukaryotes, or particles engineered to produce oxygen spontaneously or with external stimulation.

Cells from a particular disease state or genetic condition may be seeded. For example, the seed cells may be cells having an abnormality associated with a particular disease state or condition. In some embodiments the seed cells are cells derived from a tissue in an abnormal state (e.g., subsequent to a stress or trauma or event such as a myocardial infarction). Non-limiting examples of cells with particular genetic mutations or cells associated with a particular disease state or condition may include those associated with congenital cardiomyopathies, acquired cardiomyopathies, arrythmogenic cardiomyopathies (e.g., long QT syndrome, short QT syndrome (SQTS), Brugada syndrome, catecholaminergic polymorphic ventricular tachycardia (CPVT), arrythmogenic right ventricular cardiomyopathy (ARVC)), dilated cardiomyopathies (e.g., hypertrophic cardiomyopathy, left ventricular noncompaction, transthyretin amyloidosis, hereditary hemochromatosis, RASopathis (also known as Noonan spectrum disorders), heart failure, etc. In some embodiments, the disease state or condition is an acquired condition such as dilated ischemic and on-ischemic cardiomyopathies, hypertensive heart disease, etc. In some embodiments, the disease state or condition is a congenital disease acquired or congenital plus arrhythmia. In some embodiments, the disease state or condition is diabetes, a cancer, muscular dystrophy, a congenital, genetic, or acquired condition affecting the GI tract, a condition affecting skeletal muscle, smooth muscle, etc. The present invention is not limited to the aforementioned conditions.

The ECM-generating cells and/or the ECM and/or other factors of the tissue compositions may cause the differentiation and/or maturation of the seeded cells (if appropriate). Growth factors (e.g., fibroblast-derived, exogenous) may help improve one or more of: seeding, integration into the scaffold, proliferation, and differentiation of the seeded cells in vitro or in vivo. For certain cells with the ability to differentiate into two or more cell types, the microenvironment of the tissue composition (e.g., ECM-generating cells, ECM, growth factors, etc.) can help drive the pathway of differentiation. In some embodiments, exogenous factors are added to enhance differentiation in a particular direction.

The tissue compositions of the present invention may further comprise enhancement cells. Non-limiting examples of enhancement cells may include secretory cells, paracrine cells, enzymatic cells, beta cells, gastrointestinal cells, or a combination thereof. Enhancement cells may be at a particular ratio with respect to the seeded cells and/or ECM-generating cells. The ratio of the cells may depend on the cell type and a desired outcome. The ratio may also depend on clustering of the enhancement cells (e.g., cell bundles). Or, the ratio may depend on the proliferation of the cells (proliferation of the cells ultimately affects the ratio). The spheroids/embryoid bodies may be pre-fabricated or generated spontaneously in preparation. In some embodiments, the ratio of enhancement cells to seeded cells or ECM-generating cells is from 1:10 to 10:1. In some embodiments, the ratio of enhancement cells to seeded cells or ECM-generating cells is from 1:5 to 5:1. In some embodiments, the ratio of enhancement cells to seeded cells or ECM-generating cells is from 1:20 to 20:1. In some embodiments, the ratio of enhancement cells to seeded cells or ECM-generating cells is from 1:25 to 25:1. In some embodiments, the ratio of enhancement cells to seeded cells or ECM-generating cells is from 1:50 to 50:1. In some embodiments, the ratio of enhancement cells to seeded cells or ECM-generating cells is from 1:100 to 100:1. The present invention is not limited to the aforementioned ratios.

The tissue compositions of the present invention may further comprise proliferative cells different from the ECM-generating cells, e.g., adherent proliferative cells, e.g., mesenchymal stem cells, pre-vascular cells, endothelial cells, progenitor cells, etc. Note, there is a specific microenvironment for each type of cell. Thus, each cell type used would likely provide a specific niche to encourage elopement or integration of additional cell types.

As previously discussed, the seed cells may be human inducible pluripotent stem cell-derived cardiomyocytes or cardiomyocytes. In such a tissue composition, the cardiomyocytes can develop and spontaneously contract, e.g., in a synchronized manner. The cardiomyocytes allow for electrical signal propagation. In some embodiments, the scaffold directionalizes contractions. As previously discussed, in some embodiments, the fibers of the scaffold form grooves, and the grooves may help the scaffold directionalize cell seeding or contractions.

In the example with cardiomyocytes, in certain embodiments, the cardiomyocytes contract at a rate from 0 beats/min to 30 beats/min, 20 beats/min to 60 beats/min, 30 beats/min to 50 beats/min, 30 beats/min to 200 beats/min, 40 beats/min to 270 beats/min, 20 beats/min to 300 beats/min, 40 beats/min to 80 beats/min, etc. Note that factors such as but not limited to temperature, time post-cryopreservation, time post-seeding, etc. may influence beat rate. It is possible for the beat rate to be zero or to fluctuate during culture.

The seed cells may be present at a particular ratio with respect to the ECM-generating cells. The exact ratio may depend on the cell type of the seed cells. For example, in some embodiments, the ratio of seed cells to ECM-generating cells is from 1:10 to 10:1. In some embodiments, the ratio of seeded cells to ECM-generating cells is 1:1, 1:2, 1:3, 1:4, 1:5, 1:6, 1:7, 1:8, 1:9, 1:10, etc. In some embodiments, the ratio of seed cells to ECM-generating cells is from 1:5 to 5:1. In some embodiments, the ratio of seed cells to ECM-generating cells is from 1:20 to 20:1. In some embodiments, the ratio of seed cells to ECM-generating cells is from 1:25 to 25:1. In some embodiments, the ratio of seed cells to ECM-generating cells is from 1:50 to 50:1. In some embodiments, the ratio of seed cells to ECM-generating cells is from 1:100 to 100:1. In some embodiments, in a scaffold such as the hollow one of FIG. 3D, the ratio of seeded cells to ECM-generating cells is 1:1. Likewise, the amount of seed cells that are deposited on the tissue composition may depend on the cell type of the seed cell. In some embodiments, the seed cells are seeded to have a final density from $0.5 \times 10^6$ cells/cm$^2$ to $5 \times 10^6$ cells/cm2. In some embodiments, the seed cells are seeded to have a final density from $1 \times 10^4$ cells/cm$^2$ to $1 \times 10^7$ cells/cm$^2$. In some embodiments, the seed cells are seeded to have a final density from $1 \times 10^2$ cells/cm$^2$ to $1 \times 10^7$ cells/cm$^2$.

The arrangement of the seed cells may be a layer. Or, the arrangement of the seed cells on the scaffold may be in bundles, aggregates or groups of closely packed cells such as embryoid bodies, cardiospheres, etc. (or combinations of layers and bundles). The cell bundles may be of various sizes and may be mixed with single or layered cells. In certain embodiments, the tissue composition features from 3 to 500 cell layers.

In some embodiments, cell bundles (e.g., embryoid bodies) are seeded, e.g., cells are pre-clustered prior to seeding. In some embodiments, cells may form said bundles or aggregates after the seeding process. Note cells in such bundles (embryoid bodies) may exhibit their own microenvironment.

FIG. 6 shows non-limiting examples of features of seeded cells (which may include a single population of cells or a combination of populations of cells) that may be used in the three-dimensional tissue compositions herein.

Tissue Composition Features and Variations

In certain embodiments, the tissue composition comprises a biomaterial (e.g., a scaffold alone, a scaffold with seeded cells without ECM-generating cells, a scaffold with seeded cells and ECM-generating cells, a scaffold with ECM-generating cells, etc.) and a proliferative cell population. For example, the tissue composition may comprise a scaffold and ECM (with or without ECM-generating cells) and a proliferative cell population. In certain embodiments, the tissue composition comprises a biomaterial and a non-proliferative cell population. For example, the tissue composition may comprise a scaffold and ECM (with or without ECM-generating cells) and a non-proliferative cell population. The tissue compositions may have layers of cells from 3-500 cell layers thick, however the present invention is not limited to this configuration or range of cell layers. Tissue compositions herein may be cultured with factors (e.g., FGF), other proliferative cytokines, growth factors, or a combination thereof to achieve a desired thickness.

The biomaterial may be absorbable, non-absorbable, or a combination thereof. The biomaterial may feature synthetically-derived material, biologically-derived material, or a combination thereof. The biomaterial may comprise ECM-generating cells (e.g., fibroblasts) pre-seeded. In certain embodiments, the biomaterial does not comprise ECM-generating cells (e.g., fibroblasts). In certain embodiments, the biomaterial comprises pores. In certain embodiments, the biomaterial does not comprise pores. In certain embodiments, the biomaterial may feature ligands, antibodies, magnetic based particles, the like, or a combination thereof for attracting cells to the biomaterial. In certain embodiments, the culture plate, bioreactor, or other material used for producing the tissue composition may feature an anti-adhesion material on at least a portion of its surface for deterring cells from adhering to the surface and instead attaching to the biomaterial.

Non-limiting examples of proliferative cells include cardiac progenitors, fibroblasts, mesenchymal stem cells (MSCs), other progenitor cells (e.g., skeletal muscle progenitor cells, smooth muscle progenitor cells, neural progenitor cells, liver progenitor cells, etc.), and the like. Non-limiting examples of non-proliferative cells include cardiomyocytes, neural cells, pancreas cells, and the like.

Tissue compositions of the present invention, such as those made with proliferative cells, may be induced to continue to proliferate once they are seeded on the scaffold. Specific compositions (e.g., growth factors, peptides, etc.) may be used for this process. Tissue compositions of the present invention, such as those made with proliferative cells, may be allowed to proliferate on the construct and at some specified time be induced to differentiate into a specific cell type. For example, in a tissue composition comprising cardiac progenitors, the cardiac progenitors may be promoted to differentiate once the appropriate factor is introduced.

In certain embodiments, the tissue compositions (e.g., those made with proliferative cells described above) may be seeded with another cell population, e.g., endothelial cell population, cardiomyocyte population, mesenchymal stem cell (MSC) population, etc.

The tissue compositions herein may be constructed in various ways. For example, in certain embodiments, cell sheets or spheroids are generated and then subsequently transferred to the biomaterial. Cell sheets may be produced in a variety of ways. For example, cell sheets may be produced by seeding cells on a temperature sensitive plate, a low adhesion plate, or a plate with a composition (e.g., ligand) that allows for detachment of cells or tissue at a select time. Temperature-sensitive plates are designed to release adherent cells when placed at a particular temperature (e.g., between 20-25° C.). When the seeded cells have reached their appropriate confluency and/or morphology, the cells can be disassociated from the plate (e.g., temperature-sensitive plate, low adhesion plate, plate with ligand, etc.) as a sheet of cells and subsequently transferred to the biomaterial. Spheroids may be produced, for example, using centrifugation techniques, low adhesion plates, orbital shaking, etc. The spheroids can be pelleted and then seeded on to the biomaterial.

Without wishing to limit the present invention to any theory or mechanism, it is believed that the use of cell sheets or spheroids can increase the seeding efficiency of the tissue composition. This may be advantageous when working with an expensive and/or non-proliferative cell type.

The present invention also features tissue compositions constructed by seeding cells on a particular surface and subsequently adhering a biomaterial (e.g., a scaffold alone, a scaffold with seeded cells without ECM-generating cells, a scaffold with seeded cells and ECM-generating cells, a scaffold with ECM-generating cells, etc.) to the cells. Similar tissue compositions may be constructed by first adhering the biomaterial to the plate and then seeding cells. In certain embodiments, the tissue composition features layers of biomaterial and cells. Methods for adhering the biomaterial to the seeded cells may include but are not limited to centrifugation. In certain embodiments, the biomaterial comprises one or more components (e.g., ligands, etc.) for attracting the seeded cells. In certain embodiments, the seeded cells comprise one or more components (e.g., ligands) for attracting the biomaterial.

The surface may be a culture dish or culture surface with features that allow for removal of the tissue composition. For example, in some embodiments, the surface is a temperature-sensitive culture plate. The temperature-sensitive plate is designed to release adherent cells (e.g., the seeded cells of the tissue composition) when it is placed at a particular temperature (e.g., between 20-25° C.).

In certain embodiments, the plate comprises an attachment component for temporarily attaching the cells and/or biomaterial to the plate. For example, in certain embodiments the attachment component is a tuned liposome (e.g., gold-coated liposomes) with a ligand such as RGD. The ligand attaches the gold liposomes to the plate, and the cells and/or biomaterial attaches to the liposomes. When the tissue composition is ready for harvesting, the gold-coated liposomes can be activated with resonant light to open and thereby detach the tissue composition from the plate. The present invention is not limited to gold-coated liposomes. Without wishing to limit the present invention to any theory or mechanism, it is believed that one advantage to using an attachment component (such as the gold-coated liposomes) is it allows for constructing a tissue composition in a particular shape by patterning the attachment component (e.g., gold-coated liposomes) on the plate in that shape. The attachment components may also allow for stability and controlled release of cells and certain material that may be contained within the liposomes, e.g., factors required for growth and/or differentiation.

The present invention also features methods for reducing metabolic rate of tissue compositions. For example, the present invention features methods for reducing beat rates of tissue compositions, e.g., tissue compositions featuring cardiomyocytes. The methods may feature introducing a drug to the tissue composition that reduces the beat rate to a particular desired beat rate. In certain embodiments, the methods feature temperature control. In certain embodiments, the beat rate is reduced for the purpose of storage and/or stability, e.g., stability during transport. The methods for reducing the beat rate of a tissue composition may be applied to any appropriate tissue composition herein, e.g., tissue compositions featuring a scaffold, ECM, ECM-generating cells, and cardiomyocytes; tissue compositions featuring cells sheets with or without a scaffold; etc.

Furthermore, the present invention features tissue compositions (e.g., any appropriate tissue composition herein, other contractile grafts, etc.) with a beat rate from 10-20 bpm. The present invention also features tissue compositions (e.g., any appropriate tissue composition herein, other contractile grafts, etc.) with a beat rate from 20-30 bpm. The present invention also features tissue compositions (e.g., any appropriate tissue composition herein, other contractile grafts, etc.) with a beat rate from 10-30 bpm. The present invention also features tissue compositions (e.g., any appropriate tissue composition herein, other contractile grafts, etc.) with a beat rate from 30-40 bpm. The present invention also features tissue compositions (e.g., any appropriate tissue composition herein, other contractile grafts, etc.) with a beat rate from 20-40 bpm. The present invention also features tissue compositions (e.g., any appropriate tissue composition herein, other contractile grafts, etc.) with a beat rate from 40-50 bpm. The present invention also features tissue compositions (e.g., any appropriate tissue composition herein, other contractile grafts, etc.) with a beat rate from 30-50 bpm. The present invention also features tissue compositions (e.g., any appropriate tissue composition herein, other contractile grafts, etc.) with a beat rate from 0-50 bpm. The present invention also features tissue compositions (e.g., any appropriate tissue composition herein, other contractile grafts, etc.) with a beat rate from 0-100 bpm. Without wishing to limit the present invention to any theory or mechanism, it is believed that a low beat rate (e.g., a beat rate from 10-50 bpm) may be advantageous because tissue compositions with a low beat rate would have a lower metabolic burden as compared to those with a high beat rate, and the lower metabolic burden may help extend the shelf life of the tissue composition (e.g., the amount of time that the graft could be set at room temperature before being implanted). The lower metabolic burden may also be beneficial in an ischemic environment because the tissue compositions would require fewer nutrients to be healthy and functional.

Methods for modulating the beat rate of a tissue composition include but are not limited to the use of beta blockers or other exogenous factors.

The tissue compositions of the present invention are constructed to withstand short-term and/or long-term storage, e.g., cryopreservation. Cryopreservation may refer to a temperature of −80° C. to −196° C. or −90° C. to 196° C. The ability to cryopreserve the tissue composition helps allow for stocking tissues until use on demand as well as for transporting the tissue compositions from one location to another.

The tissue compositions may also be constructed to withstand certain lengths of time at room temperature (or a temperature below 37° C.). The ability to remain viable at a temperature below 37° C. for certain lengths of time may be beneficial for instances when the tissue composition is out of the incubator prior to use. As an example, a tissue composition may be exposed to room temperature for a lengthy period of time when it is removed from the incubator, brought to an operating room for use in an implantation process, but is not implanted immediately.

Properties of the Tissue Composition

The engineered tissue compositions of the present invention (e.g., featuring cardiomyocytes) can be evaluated for one or more mechanical parameters, electrophysiological parameters, chemical parameters, biochemical parameters (growth factors, metabolites, ion channels, etc.), or a combination thereof. Mechanical parameters or electrophysiological parameters may include but are not limited to contraction rate, contraction/relaxation velocity, force of contraction-paced, force of contraction—not paced, displacement velocity, displacement force, directionality of impulse, velocity of impulse, field potential, amplitude, capture threshold, chronotropic response, activation sequence after stimulation, functional gap junction formation, response to electrical pacing, field potential amplitude, conduction velocity, propagation patterns, gap junction analysis, or a combination thereof.

Likewise, the engineered tissue composition (e.g., featuring cardiomyocytes) can be subjected to multi-electrode array mapping for real-time electrophysiology measurements. Contraction rate, systolic/diastolic displacement, systolic contraction velocity, and/or diastolic relaxation velocity may be detected with a microscope. As previously discussed, the cardiomyocytes can be paced. Pacing may be achieved by external field stimulation applied.

The tissue composition, for example a tissue composition comprising cardiomyocytes, may be constructed to have a particular beat rate. In certain embodiments, the beat rate is from 0-100 beats per minute (bpm). In certain embodiments, the beat rate is from 10 to 30 bpm. In certain embodiments, the beat rate is from 20 to 40 bpm. In certain embodiments, the beat rate is from 30 to 60 bpm. In certain embodiments, the beat rate is from 40 to 70 bpm. In certain embodiments, the beat rate is from 50 to 80 bpm. In certain embodiments, the beat rate is from 60 to 90 bpm. In certain embodiments, the beat rate is from 70 to 100 bpm. The present invention is not limited to the aforementioned examples of beat rates.

The mechanical properties of the engineered tissue composition (e.g., featuring cardiomyocytes) may depend on the scaffold material used. For example, displacement, strain percentage, displacement velocity, etc., may all depend on the material of the scaffold. In some embodiments, the engineered tissue composition (e.g., featuring cardiomyocytes) has a voltage amplitude across the engineered tissue composition from 0.1 mV to 1 mV with inter-electrode spacing of 1 mm-1.5 cm.

The tensile strength of the tissue composition can be determined by its composition, e.g., the percentage of scaffold, ECM, cells, etc.

In certain embodiments, the relative expression of a marker can be evaluated to determine the amount of a particular cell type of interest (e.g., cardiomyocyte, skeletal muscle cell, smooth muscle cell, etc.) relative to the ECM-generating cells (e.g., fibroblast). The ratio of the cell type of interest to the ECM-generating cells will change over time based on the changes of the tissue composition, e.g., if the cells of interest proliferate, if certain cell populations die, if cells differentiate over time, etc. Non-limiting examples of markers that may be evaluated include CD90, vimentin, FSP-1, collagen I, alpha-SMA, HSP47, etc.

Platforms

The present invention also features platforms with the tissue compositions of the present invention. For example, the present invention features a single-well plate (with a single well), wherein an engineered tissue composition of the present invention is deposited in the well therein. The present invention also features multi-well plate with two or more wells, wherein an engineered tissue composition of the present invention is deposited in at least one well therein. The multi-well plate may comprise two wells, four wells, six wells, eight wells, 12 wells, 24 wells, 48 wells, 96 wells, more than 96 wells, from 2 to 12 wells, from 12 to 24 well, from 24 to 48 wells, from 48 to 96 wells, etc. The present invention also features platforms for the engineered tissue composition comprising wells within wells, troughs, or any other appropriate culture apparatus such as a tube, tray, etc. The present invention is not limited to a culture dish as a platform for culturing, maintaining, and/or storing the tissue compositions.

The present invention also features closed system platforms for producing, maintaining, and/or storing the tissue compositions herein. For example, the closed system may feature an encapsulation with the tissue composition, e.g., the scaffold and ECM and optionally other components as discussed herein, housed therein. Media can be exchanged in the closed system in a sterile manner. The tissue compositions can also be frozen in the encapsulation and thawed when ready. In certain embodiments, more than one tissue composition can be housed in the encapsulation or multiple encapsulations can be connected together to create a new encapsulation. For example, in some embodiments, up to 6 tissue compositions are housed in the encapsulation. In some embodiments, up to 10 tissue compositions are housed in the encapsulation. In some embodiments, up to 20 tissue compositions are housed in the encapsulation. In some embodiments, more than 20 compositions are housed in the encapsulation.

Methods of Use

The tissue compositions of the present invention may be used for a variety of purposes, e.g., in vivo uses, in vitro uses, e.g., implantation into a patient, in vitro assays, cell differentiation platforms, etc. For example, the present invention features methods for repairing tissue (e.g., tissue having been affected by a disease or condition, trauma, etc.), wherein a tissue composition of the present invention is implanted into the affected tissue to enhance the function of the affected tissue. As a non-limiting example, a cardiac tissue composition (featuring cardiomyocytes) may be implanted into cardiac tissue of interest, wherein the engineered tissue composition enhances function of the cardiac tissue. A disease or condition may include (but is not limited to) arrhythmia, heart failure, myocardial infarction, Arrhythmogenic cardiomyopathies (e.g., Long QT syndrome (LQTS), Short QT syndrome (SQTS), Brugada syndrome, Catecholaminergic polymorphic ventricular tachycardia (CPVT), Arrhythmogenic right ventricular cardiomyopathy (ARVC), Dilated Cardiomyopathies (e.g., Hypertrophic Cardiomyopathy, Left Ventricular Noncompaction, Transthyretin Amyloidosis, Hereditary Hemochromatosis, RASopathies (also known as Noonan spectrum disorders)), any other acquired form of heart disease or injury, or any other congenital form of heart disease or injury.

The present invention also features methods for differentiating a cell by seeding said cell on an engineered tissue composition of the present invention. Compounds from the ECM-generating cells of the tissue composition or other factors therein cause differentiation of the cell. The present invention also features methods for enhancing maturation of a cell by seeding said cell on an engineered tissue composition of the present invention. Compounds from the ECM-generating cells of the tissue composition or other factors therein may cause maturation of the cell. The present invention also features methods for driving a particular phenotype or genotype of a cell by seeding said cell on an engineered tissue composition of the present invention. Compounds from the ECM-generating cells of the tissue composition or other factors therein may cause development of the cell to express a particular phenotype or genotype.

Note that the tissue composition of the present invention (e.g., the microenvironment, e.g., the compounds from the ECM-generating cells) may result in the generation/differentiation of the seeded cells into multiple different cell populations with varying ratios. For example, a group of progenitor cells may differentiate into two or more cell populations. As another example, seed cells may differentiate into cardiomyocytes (e.g., 80-90%), endothelial cells (e.g., 2-10%), and smooth muscle cells (e.g., 2-10%).

The tissue compositions of the present invention may also be used for implantation. Methods may feature open surgical procedures, minimally invasive procedures, percutaneous procedures, robotic procedures, etc.

The methods and compositions herein may be used for various subjects, e.g., humans/primates, pigs, rats, dogs, horses, cats, etc.

Since the engineered tissue compositions of the present invention may mimic native tissue, the engineered tissue compositions may be used for testing compounds or other components in an effort to detect harmful or toxic effects, or for detecting beneficial or therapeutic effects. For example, the present invention features methods for method of detecting effects (e.g., harmful, toxic, beneficial, therapeutic) of a test component (e.g., drug, small molecule, cell, cell product, etc.) on a particular tissue, e.g., the tissue of the engineered tissue compositions. The tissue, for example, may be cardiac tissue. In some embodiments, the method comprises introducing the test component to the engineered tissue composition. In some embodiments, the engineered tissue composition is stimulated in some way. The method may further comprise measuring one or more physical parameters, mechanical parameters, electrophysiological parameters, biochemical parameters, or the like. Depending on the result of the test, it may be determined whether or not the test component has a harmful or beneficial effect. In some embodiments, the method further comprises measuring displacement, strain, force, conduction velocity, milivoltage amplitude, or a combination thereof.

Directionality of impulse is measured using at least two distinct electrodes (along the x-axis or along the y-axis). The sequence of activation can be determined, and therefore directionality of impulse can be determined. Velocity of impulse is measured using at least two distinct electrodes (along the x-axis or along the y-axis). Field Potential is measured using the unipolar electrogram tracings from individual electrodes, or by combining electrodes to form a bipolar tracing. The voltage/field potential can be recorded, and amplitude can be subsequently analyzed. Capture threshold is measured using proprietary software that Inventors developed. The constructs can be stimulated at specific locations through the multi-electrode array, and the minimum voltage necessary to cause depolarization of the construct's network of cells can be determined. Chronotropic response is measured using the same proprietary software that Inventors developed. The heart can be stimulated at a determined rate and monitored for the response. The tissue composition (e.g., graft) can be stimulated in a known location and the subsequent activation of the construct along multiple axes can be recorded. Inducibility of sustained ventricular tachycardia can be measured by pacing and introducing a programmed extra stimulus.

Example 1

Example 1 describes an example of a method for producing a tissue composition of the present invention. The present invention is not limited to the features of this example herein. (1) Human dermal fibroblasts (HDFs) are removed from liquid nitrogen, warmed, and cultured in a culture dish. (2) The HDFs are passaged about 8 times (can be passaged up to about 20 passages), each passage taking place when the cells are at about 80% confluency. (3) At the appropriate passage, the cells are harvested (cells may be removed from the culture dish via trypsin or the like, or the cells may be scraped). (4) A scaffold is placed in a tissue culture dish (e.g., 60 mm dish). Note the scaffold may be any appropriate shape and size, and the tissue culture dish is not limited to a round 60 mm dish. For example, the scaffold and dish may be rectangular, square, etc. (5) The HDFs are applied to the scaffold. The number of cells (and volume, thus concentration of cells) is known. Note, a cryopreserved vial of HDFs can be warmed and seeded directly on the scaffold without passaging. (6) Gravity, rocking, and/or centrifugation may be used for seeding the HDFs. (7) Scaffold-HDF cultures may be cultured for a particular length of time, e.g., 30 days. When the fibroblasts appear ready, another population of cells (e.g., seeded cells such as cardiomyocytes) can be seeded, e.g., using centrifugation. (8) Seeded cells may be cultured on the tissue composition for a particular length of time, e.g., 2 days. (9) Tissue compositions can optionally be cryopreserved (e.g., using a controlled rate freezing protocol), or the tissue compositions can immediately be used for various purposes, e.g., surgical implantation, in vitro drug studies, etc., as described herein.

Example 2

Figure 7A:
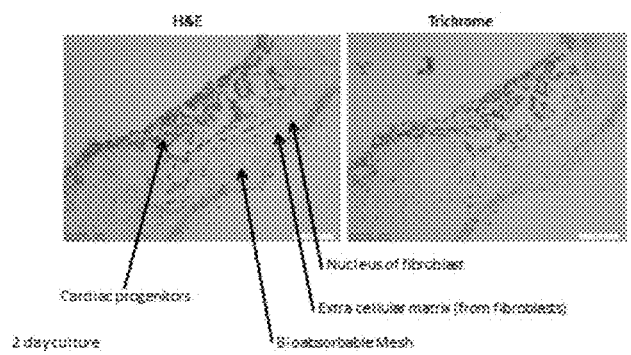
FIG. 7A shows the cardiac cell layer of a tissue composition of the present invention stained with H&E (left panel) and trichrome (right panel) (see Example 2). Cardiac progenitors (CPCs) were cultured into tissue compositions of the present invention. In contrast to terminally differentiated cardiomyocytes, the cardiac progenitors are proliferative and generate thick layers of cells, e.g., approximately 20-100 cells thick.
Figure 7B:
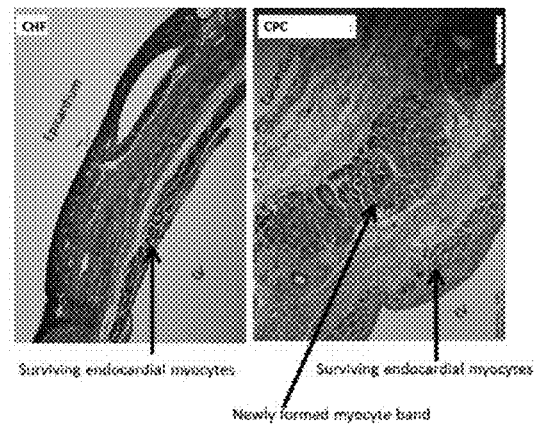
FIG. 7B shows images of ventricular anterior walls following implantation of the graft (tissue composition) of FIG. 7A into a rodent model of chronic heart failure (CHF). Left ventricular cross sectional analysis was performed of untreated CHF rats (left panel) and CHF rats treated with cardiac progenitor grafts (right panel) using Masson's Trichrome stain. Untreated CHF rats have thinner left ventricular anterior walls, e.g., scar area with few surviving myocytes. After treatment with cardiac progenitor cell grafts, the anterior wall/scar is thicker with increased myocyte density demonstrated by the increased positive red staining.
Figure 7C:
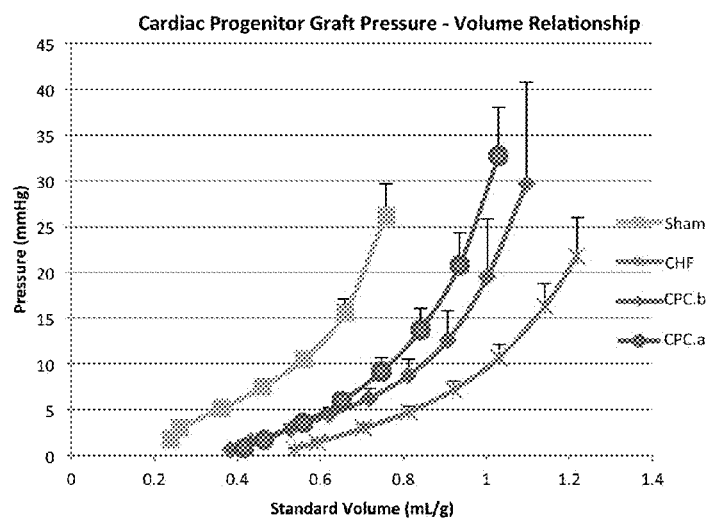
FIG. 7C shows diastolic pressure volume relationship curves after implantation of the graft (tissue composition) of FIG. 7A into a rodent model of chronic heart failure (CHF). Ex-vivo diastolic pressure volume relationship curves were performed in CHF, n=9; CPC.a and CPC.b, n=4 groups. Both CPC.a and CPC.b grafts shift pressure volume relationship back towards normal. Thus graft treated animals operated at a lower LV end-diastolic pressure (EDP) for any given volume. This lower EDP would be assumed to have a beneficial effect on patient symptoms in heart failure such as shortness of breath. Additionally, these data demonstrate in this instance there were no negative consequences of graft implantation such as cardio-restriction. Data are mean±SE. CHF=Chronic heart failure, CPC=cardiac progenitor.

Example 2 describes a tissue composition of the present invention. The present invention is not limited to the methods and features described in Example 2. A study was performed with cardiac progenitor cells. Inventors surprisingly found that the cardiac cell layer within the constructs (tissue compositions) is much thicker than previously described, e.g., the cell layer was from 1-50 cells (see FIG. 7A). The cardiac progenitors are proliferative and continue to replicate during the culture period. Implantation of this graft (tissue composition) into a rodent model of chronic heart failure (CHF) resulted in improvements in cardiac function (see FIG. 7B, FIG. 7C, and Table 1, Table 2, and Table 3). In some embodiments, the tissue compositions of the present invention are allogeneic cryopreserved cardiac grafts, which may be implanted on the epicardium of the heart. Some data has shown that these grafts can decrease susceptibility to ventricular tachycardia. In addition, these progenitor cells have the capability of differentiating into cardiac specific mesoderm lineage cells (endothelial, smooth muscle, and cardiomyocytes). Without wishing to limit the present invention to any theory or mechanism, it is possible that the growth factor milieu of the fibroblast graft helps drive and direct differentiation of the cardiac cells in vitro.

As previously discussed, it was surprising that the cells would continue to divide after implantation. Without wishing to limit the present invention to any theory or mechanism, it is hypothesized that cardiac progenitor cells may have a greater resistivity to hypoxia and may survive in hypoxic or post infarcted environments better then terminally differentiated cardiomyocytes. The grafts final cell ratios are 5:1 to 100:1.

Referring to Table 1, Hemodynamic evaluations were performed at the end of study in Sham, CHF and CPC (hiPSC derived cardiac progenitor) treated progenitor cell grafts using solid state Millar catheters. Implantation of cardiac progenitor cardiac grafts result in decreased EDP, and Tau while increasing PDP. These values result in improved filling capabilities of the heart and ultimately suggest patients treated with these grafts may feel better resulting in reduction of New York Heart Class classification. Data are mean±SEM. CHF, n=6; Sham, n=10; CPC, n=13. Abbreviations: HR=Heart Rate, EDP=End Diastolic Pressure, SysP=Systolic Pressure, dP/dt=change in pressure over time, PDP=Peak Developed Pressure, CHF=Chronic Heart Failure.

TABLE 1

Hemodynamic assessment 7 wks post progenitor cell graft treatment

|      | HR bpm   | EDP mmHg | SysP mmHg | dP/dt(−) mmHg/sec | dP/dt(+) mmHg/sec | Tau msec | PDP mmHg |
|------|----------|----------|-----------|-------------------|-------------------|----------|----------|
| Sham | 297 ± 24 | 6 ± 1    | 128 ± 4   | 6368 ± 468        | 7146 ± 285        | 20 ± 4   | 171 ± 5  |
| CHF  | 250 ± 12 | 24 ± 6   | 118 ± 7   | 3190 ± 465        | 4733 ± 627        | 37 ± 5   | 132 ± 14 |
| CPC  | 246 ± 8  | 14 ± 3   | 123 ± 5   | 3815 ± 406        | 5302 ± 374        | 33 ± 2   | 155 ± 8  |

Referring to Table 2, Noninvasive echocardiographic evaluations were performed at three weeks post treatment. Implantation of a cardiac progenitor cell graft result in increased EF and FS with reductions in maladaptive remodeling (LVid-sys/dia and LVv-sys/dia). Data are mean±SE. CHF, n=6; CPC. Abbreviations: EF=Ejection Fraction; FS=Fractional Shortening; sys=Systolic; dia=Diastolic; LVid=Left Ventricular Interior Dimension; LVv=Left Ventricular Volume; AW=Anterior Wall.

TABLE 2

Echocardiographic assessments 3 wk post progenitor cell graft treatment

|     | EF %     | FS %     | LVid-sys mm | LVid-dia mm | LVv-sys uL  | LVv-dia uL  | AWsys mm  |
|-----|----------|----------|-------------|-------------|-------------|-------------|-----------|
| CHF | 28 ± 3.8 | 15 ± 1.8 | 9 ± 0.5     | 10 ± 0.5    | 421 ± 47.0  | 592 ± 62.2  | 1.6 ± 0.2 |
| CPC | 32 ± 4.6 | 16 ± 5.5 | 8 ± 0.6     | 10 ± 0.4    | 412 ± 55.0  | 570 ± 51.9  | 1.7 ± 1.2 |

Referring to Table 3, Noninvasive echocardiographic evaluations were performed at three weeks post treatment. Implantation of a cardiac progenitor cell graft result in increased EF and FS with reductions in maladaptive remodeling (LVid-sys/dia and LVv-sys/dia). Data are mean±SE. CHF, n=6; CPC. Abbreviations: EF=Ejection Fraction; FS=Fractional Shortening; sys=Systolic; dia=Diastolic; LVid=Left Ventricular Interior Dimension; LVv=Left Ventricular Volume; AW=Anterior Wall.

TABLE 3

Echocardiographic assessments 7 wk post progenitor cell graft treatment

|     | EF %     | FS %     | LVid-sys mm | LVid-dia mm | LVv-sys uL  | LVv-dia uL  | AWsys mm  |
|-----|----------|----------|-------------|-------------|-------------|-------------|-----------|
| CHF | 26 ± 3.2 | 12 ± 1.4 | 10 ± 0.4    | 11 ± 0.4    | 516 ± 48.0  | 682 ± 47.2  | 1.5 ± 0.1 |
| CPC | 32 ± 4.6 | 17 ± 2.7 | 8 ± 0.5     | 10 ± 0.4    | 410 ± 50.6  | 575 ± 45.2  | 1.9 ± 0.1 |

Example 3

Example 3 describes a tissue composition of the present invention. The present invention is not limited to the methods and features described in Example 3. Example 3 describes a slower degrading mesh scaffold seeded with fibroblasts and cardiomyocytes and evaluated for functional benefit in rats with heart failure. The tissue composition was also cryopreserved and reconstituted before implantation. The data shows function improvement after implant and between 3 and 7 weeks post implant.

Figure 8A:
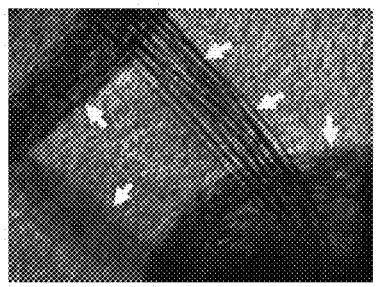
FIG. 8A shows a 10× magnification photomicrograph of a tissue composition of the present invention (described in Example 3), wherein hiPSC-CMs and hNDFs fill pores of a bio-absorbable mesh. The mesh fibers are denoted by the white arrows. The cells fill the mesh pores and generate an intact syncytium that beats spontaneously and synchronously and can be easily handled by the surgeon.

Tissue compositions (hiPSC-CM grafts) (1.7 cm diameter) were manufactured by culturing human dermal fibroblasts (hNDF) and human iPSC derived cardiomyocytes (hiPSC-CMs) into a bioabsorbable mesh (see FIG. 8A). Grafts were cryopreserved at −196° C. for 2-4 weeks, thawed, reconstituted and implanted into rats with CHF. Myocardial infarctions (MI) were generated in immune competent rats by permanently ligating the left coronary artery (LCA) (Time=0). The rats recovered for three weeks to develop chronic heart failure. Then, the tissue composition (hiPSC-CM graft) was implanted (Time=3 weeks) via median sternotomy. Echocardiography was performed 3, 6 and 10 weeks post infarct (0, 3 and 7 weeks post graft implantation). Hemodynamics and ex-vivo pressure volume cures were obtained at study endpoint (study endpoint Time=10 weeks).

Figure 8B:
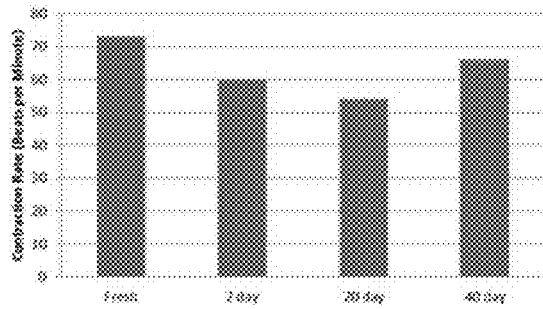
FIG. 8B shows the effects of cryopreservation on the tissue composition used in Example 3. Fresh vs. 2, 20, and 40 day post-thaw contraction rates were recorded. While previously frozen tissue compositions (hiPSC-CM graft) had slightly slower contraction rates, the tissue compositions still displayed synchronous and spontaneous contractions. Fresh, n=6; 2, 20, 40 day n=1.
Figure 8C:
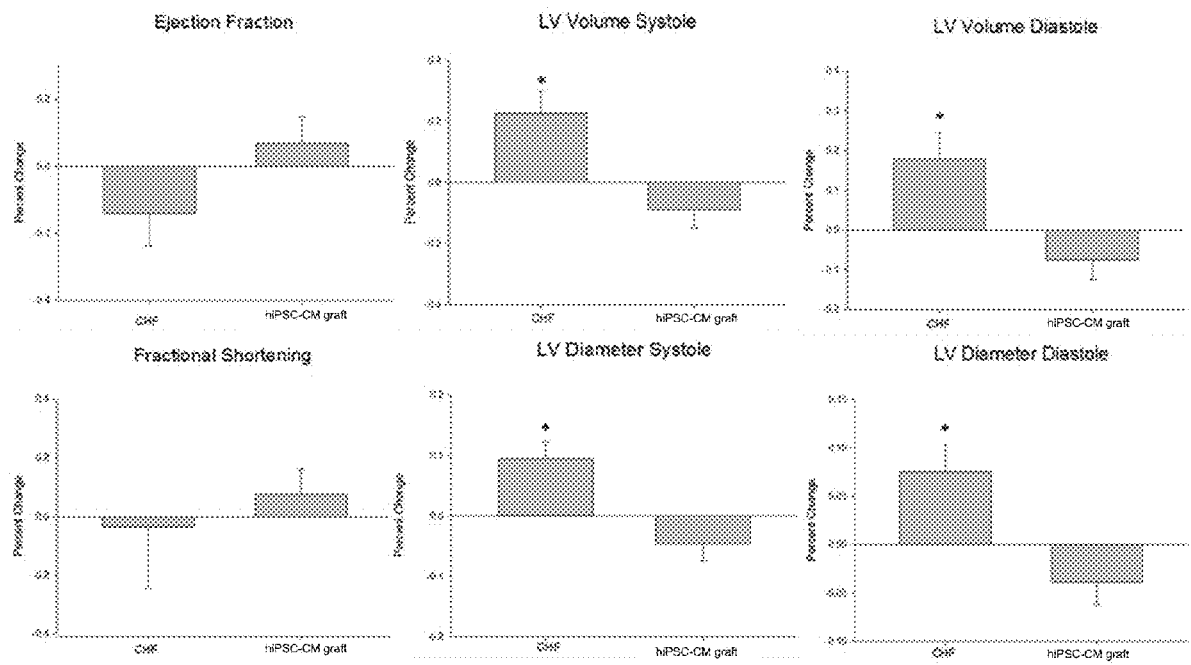
FIG. 8C shows echocardiographic evaluations performed at 3 and 7 weeks after implantation of the tissue composition in Example 3 (hiPSC-CM graft). The tissue composition decreases LV size and volume as compared to CHF controls. Data are mean±SE of percent change between 3 and 7 weeks. * denotes statistical difference (p<0.05) between CHF and hiPSC-CM graft. CHF, n=6; hiPSC-CM graft, n=10.
Figure 8D:
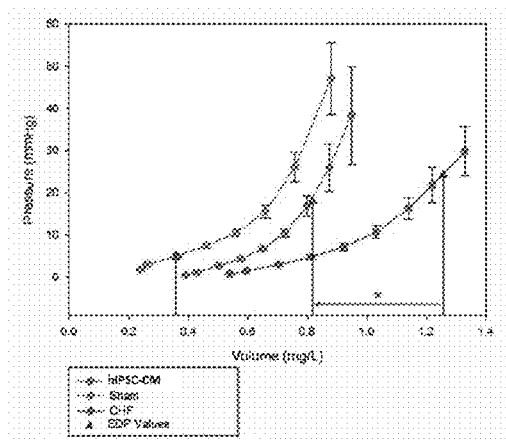
FIG. 8D shows ex-vivo pressure volume relations were performed via langendorff preparation. CHF shifts the pressure volume relation to the right. Treatment with the tissue composition in Example 3 (hiPSC-CM graft) shifts the pressure volume curve left back towards the pressure axis. The leftward shift results in a decrease in end diastolic operating pressure. Sham, n=6; CHF, n=6; hiPSC-CM graft, n=2.

The tissue composition of the present invention used herein (hiPSC-CM graft) maintained spontaneous and synchronous contractions pre-freeze (65±10 bpm) and post thaw (60±10 bpm). Grafts were maintained out to 40 days post thaw with no deterioration in composition or beat rate (see FIG. 8B). The tissue composition used (hiPSC-CM graft) reversed maladaptive left ventricular (LV) remodeling by decreasing (p<0.05) LV volume systole/diastole, LV diameter systole/diastole with trending improvement in ejection fraction and fractional shortening from 3 and 7 weeks post implantation as compared to CHF controls (see FIG. 8C). Grafts decreased LV end diastolic pressure, 24±6 mmHg (CHF control) vs. 18±3 mmHg (tissue composition used) and showed trending improvements in LV dP/dt(−) and dP/dt(+) as compared to controls (see Table 4; Hemodynamics evaluations were performed at study endpoint (7 weeks after hiPSC-CM graft implant, 10 weeks after MI). hiPSC-CM graft improved LV EDP and shows trending improvements of dP/dt(+). Sham, n=6; CHF, n=6; hiPSC-CM graft, n=10). In addition, the tissue composition used (hiPSC-CM graft) results in 36% reduction in LV EDP operating volume as demonstrated by a leftward shift of the diastolic pressure-volume relationship (see FIG. 8D).

TABLE 4

|  | HR bpm | EDP mmHg | SysP mmHg | dP/dt(−) mmHg/sec | dP/dt(+) mmHg/sec | Tau msec | PDP mmHg |
|---|---|---|---|---|---|---|---|
| Sham | 297 ± 24 | 6 ± 1 | 128 ± 4 | 6368 ± 468 | 7146 ± 285 | 20 ± 4 | 171 ± 5 |
| CHF | 250 ± 12 | 24 ± 6 | 118 ± 7 | 3190 ± 465 | 4733 ± 627 | 37 ± 5 | 132 ± 14 |
| hiPSC-CM | 251 ± 10 | 18 ± 3 | 129 ± 6 | 3575 ± 450 | 5422 ± 397 | 37 ± 3 | 140 ± 8 |

Example 3 shows the tissue composition of the present invention could be cryopreserved, reconstituted and implanted in rats with CHF. Treated rats demonstrated reversal of maladaptive LV remodeling and continued functional improvement from 3 to 7 weeks post treatment. Without wishing to limit the present invention to any theory or mechanism, it is believed that the ability to cryopreserve will allow long-term storage after large batch manufacture, thereby providing cost and utility advantages.

The disclosures of the following U.S. patents are incorporated in their entirety by reference herein: U.S. Pat. No. 4,963,489; U.S. Pat. App. No. US2009/0269316; WO2013151755; WO2011102991; U.S. Pat. App. No. 2014/0178450; U.S. Pat. No. 8,802,144; WO2009102967; U.S. Pat. No. 9,119,831; WO2010042856; U.S. Pat. No. 2008/0075750. U.S. Pat. No. 9,587,222.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A tissue composition for implantation onto cardiac tissue, said tissue composition comprising:
   a. a scaffold having a flat orientation comprising a first fiber type and a second fiber type in a knitted or woven configuration with pores therein, the first fiber type comprising glycolide, lactide, and trimethylene carbonate and the second fiber type comprising lactide and trimethylene carbonate, the first fiber type having a degradation profile different from that of the second fiber type;
   b. extracellular matrix (ECM)-generating cells and ECM incorporated on the scaffold or on and within the scaffold;
   c. inducible pluripotent stem cell-derived cardiomyocytes, pluripotent stem cell-derived cardiomyocytes, cardiac progenitor cells, or cardiomyocytes therein and forming an intact syncytium.

2. The composition of claim 1, wherein the inducible pluripotent stem cell-derived cardiomyocytes, pluripotent stem cell-derived cardiomyocytes, cardiac progenitor cells, or cardiomyocytes are 20-100 cells thick.

3. The composition of claim 1, wherein the ECM-generating cells are at a density from $1 \times 10^4$ to $1 \times 10^8$ cells/cm$^2$.

4. The composition of claim 1, wherein at least 75% of the pores are filled in by the ECM-generating cells and ECM.

5. The tissue composition of claim 1, wherein the inducible pluripotent stem cell-derived cardiomyocytes, pluripotent stem cell-derived cardiomyocytes, cardiac progenitor cells, or cardiomyocytes are at a density from $1 \times 10^2$ to $1 \times 10^7$ cells/cm$^2$.

6. The composition of claim 1, wherein the scaffold comprises 40% by weight of the first fiber and 60% by weight of the second fiber.

7. The composition of claim 1, wherein the pores have a diameter from 500 μm to 1500 μm.

* * * * *